(12) United States Patent (10) Patent No.: US 8,471,210 B2
Scoullar et al. (45) Date of Patent: Jun. 25, 2013

(54) RADIATION IMAGING METHOD WITH INDIVIDUAL SIGNAL RESOLUTION

(75) Inventors: Paul Andrew Basil Scoullar, Fitzroy North (AU); Robin John Evans, Aspendale (AU); Christopher Charles McLean, Kangaroo Flat (AU)

(73) Assignee: Southern Innovation International Pty Ltd., Carlton North, Victoria (AU)

( * ) Notice: Subject to any disclaimer, the term of this patent is extended or adjusted under 35 U.S.C. 154(b) by 111 days.

(21) Appl. No.: 12/935,588

(22) PCT Filed: Mar. 31, 2009

(86) PCT No.: PCT/AU2009/000395
§ 371 (c)(1),
(2), (4) Date: Dec. 23, 2010

(87) PCT Pub. No.: WO2009/121132
PCT Pub. Date: Oct. 8, 2009

(65) Prior Publication Data
US 2011/0147594 A1 Jun. 23, 2011

Related U.S. Application Data

(60) Provisional application No. 61/041,144, filed on Mar. 31, 2008, provisional application No. 61/138,879, filed on Dec. 18, 2008.

(51) Int. Cl.
*G01T 1/20* (2006.01)
(52) U.S. Cl.
USPC .......................................................... 250/362

(58) Field of Classification Search
USPC ........................................................ 250/362
See application file for complete search history.

(56) References Cited

U.S. PATENT DOCUMENTS

| | | | |
|---|---|---|---|
| 4,658,216 | A | 4/1987 | Goulding et al. |
| 5,210,423 | A | 5/1993 | Arseneau |
| 5,225,682 | A | 7/1993 | Britton et al. |
| 5,349,193 | A | 9/1994 | Mott et al. |
| 5,349,195 | A | 9/1994 | Dumont |

(Continued)

FOREIGN PATENT DOCUMENTS

| | | |
|---|---|---|
| CN | 101666227 | 3/2010 |
| JP | 10186041 | 7/1998 |

(Continued)

OTHER PUBLICATIONS

Golub et al., Matrix Computations, The Johns Hopkins University Press, (1989), $2^{nd}$ Ed.—TOC only.

(Continued)

*Primary Examiner* — Marcus Taningco
(74) *Attorney, Agent, or Firm* — Knobbe Martens Olson & Bear LLP

(57) ABSTRACT

An imaging method and apparatus are provided. The method includes collecting detector output data from a radiation detector positioned near a subject provided with a radioactive tracer The method further includes resolving individual signals in the detector output data by determining a signal form of signals present in the data, and making parameter estimates of one or more parameters of the signal. The one or more parameters include at least a signal temporal position. The method further includes determining the energy of each of the signals from at least the signal form and the parameter estimates.

32 Claims, 18 Drawing Sheets

U.S. PATENT DOCUMENTS

| | | |
|---|---|---|
| 5,532,944 A | 7/1996 | Battista |
| 5,884,234 A | 3/1999 | Jorion et al. |
| 6,057,551 A | 5/2000 | Tararine |
| 6,160,259 A | 12/2000 | Petrillo et al. |
| 6,215,122 B1 | 4/2001 | Clifford et al. |
| 6,590,957 B1 | 7/2003 | Grudberg et al. |
| 7,139,350 B2 | 11/2006 | Tiller et al. |
| 7,439,515 B2 | 10/2008 | Bak |
| 7,725,281 B2 | 5/2010 | Jordanov |
| 7,763,859 B2 | 7/2010 | Mott |
| 7,817,762 B2 | 10/2010 | Johnstone et al. |
| 7,999,220 B2 | 8/2011 | Odom |
| 8,227,761 B2 | 7/2012 | Zhu et al. |
| 2003/0033097 A1* | 2/2003 | Tanaka et al. ............. 702/60 |
| 2004/0195512 A1* | 10/2004 | Crosetto ............. 250/363.04 |
| 2006/0157655 A1* | 7/2006 | Mammone et al. ........... 250/395 |
| 2006/0284100 A1* | 12/2006 | Bak ............. 250/369 |
| 2007/0147702 A1* | 6/2007 | Scoullar et al. ............. 382/276 |
| 2009/0127467 A1* | 5/2009 | Frach ............. 250/363.03 |
| 2010/0074397 A1 | 3/2010 | Kappler et al. |
| 2010/0270473 A1 | 10/2010 | Kraft et al. |

FOREIGN PATENT DOCUMENTS

| | | |
|---|---|---|
| JP | 2001337168 | 12/2001 |
| JP | 3836629 B2 | 10/2006 |
| JP | 3907910 B2 | 4/2007 |
| JP | 3980451 B2 | 9/2007 |
| JP | 2009229127 | 10/2009 |
| JP | 4358814 B2 | 11/2009 |
| JP | 4706566 B2 | 6/2011 |
| JP | 4787989 B2 | 10/2011 |
| KR | 20110120015 | 11/2011 |
| WO | WO 94/28438 | 12/1994 |
| WO | WO 97/07591 | 2/1997 |
| WO | WO 99/58999 | 11/1999 |
| WO | WO 00/39600 | 7/2000 |
| WO | WO 02/097471 | 12/2002 |
| WO | WO 03/040757 | 5/2003 |
| WO | WO 2005/121835 | 12/2005 |
| WO | WO 2005/121988 | 12/2005 |
| WO | WO 2006/029475 | 3/2006 |
| WO | WO 2007/015198 | 2/2007 |
| WO | WO 2007/049168 | 5/2007 |
| WO | WO 2007/146350 | 12/2007 |
| WO | WO 2008/089014 | 7/2008 |
| WO | WO 2008/155679 | 12/2008 |
| WO | WO 2009/020863 | 2/2009 |
| WO | WO 2009/020866 | 2/2009 |
| WO | WO 2009/032452 | 3/2009 |
| WO | WO 2009/050619 | 4/2009 |
| WO | WO 2009/059312 | 5/2009 |
| WO | WO 2009/076256 | 6/2009 |
| WO | WO 2010/014576 | 2/2010 |
| WO | WO 2011/002452 | 1/2011 |
| WO | WO 2011/023431 | 3/2011 |
| WO | WO 2011/039312 | 4/2011 |
| WO | WO 2012/029496 | 3/2012 |
| WO | WO 2012/088781 | 7/2012 |

OTHER PUBLICATIONS

Haykin, S., Adaptive Filter Theory, Pearson Prentice Hall (2002), 4$^{th}$ Ed.—TOC only.

Meng et al., An Inter-comparison ray Spectroscopy, IEEE Transact of Three Spectral-Deconvolution Algorithms for Gamma-ray Spectroscopy, IEEE Transact Nucl Science (Aug. 2000) 47(4): 1329-1336.

International Search Report dated May 14, 2009 for Application No. PCT/AU2009/000395, filed Mar. 31, 2009.

International Preliminary Report on Patentability dated Oct. 5, 2010 for International Application No. PCT/AU2009/000395, filed Mar. 31, 2009.

* cited by examiner

RADIATION IMAGING METHOD WITH INDIVIDUAL SIGNAL RESOLUTION

RELATED APPLICATION

This application is based on and claims the benefit of the filing date of U.S. application No. 61/041,144 filed 31 Mar. 2008 and of U.S. application No. 61/138,879 filed 18 Dec. 2008, the contents of which as filed are incorporated herein by reference in their entirety.

FIELD OF THE INVENTION

The present invention relates generally to an imaging method and apparatus, of particular but by no means exclusive application in medical imaging techniques such as Single Photon Emission Computed Tomography (SPECT), Positron Emission Tomography (PET) and gamma-camera imaging.

BACKGROUND OF THE INVENTION

Molecular Imaging is emerging as a powerful and sensitive technique for functional imaging of the biological functions of the human body. In particular Single Photon Emission Computed Tomography (SPECT) and Positron Emission Tomography (PET) are two of the most effective technologies for the detection and staging of cancer.

In these techniques, tracers comprising compounds—such as simple sugars—labeled with radiation-emitting radio-pharmaceutical compounds are injected into the patient. The radiation gives rise to gamma-rays that are detected and recorded as the tracer travels through the body and collect in the organs targeted for examination. Cancer cells metabolise sugar at higher rates than normal cells, and the radio-pharmaceutical is drawn in higher concentrations to cancerous areas.

Gamma-ray detectors are used to detect radiation emitted from within the patient. The radiation is created when isotropically emitted positrons slow down and interact with electrons in the tissue and are annihilated. The annihilation of electron and positron produces two 511 keV gamma-rays that are emitted in opposite directions, that is, directions essentially 180° apart. The gamma-ray photons are detected in coincidence using opposing detectors.

When two gamma-rays of the correct energy are detected in coincidence and identified, computed tomography algorithms are used to reassemble each of these valid events into images. In order validly to detect a coincidence event, however, the opposing 511 keV gamma-ray must: (1) be detected in opposing detectors within a narrow time window, $\Delta t$; and (2) must have the correct energy, that is 511 keV$\pm\Delta E$, where $\Delta E$ is typically 10% or ~50 keV. Higher numbers of false coincidences are detected if $\Delta t$ and/or $\Delta E$ is increased, but excessively protracted measurement time (or tracer dose) becomes necessary if count rate is too small, owing to excessively small $\Delta t$ or $\Delta E$.

The gamma-ray detectors used in PET machines have a finite response time to incoming radiation events. Owing to the random nature of the radiation emission from the patient, more than one radiation event may arrive at the detector within the finite response time of the detector. This phenomenon is known as pulse pile-up; when it occurs, it is not possible accurately to determine either the time of arrival of the event nor the energy of the radiation event as one event is corrupted by the arrival of the next event. Thus, when pulse pile-up occurs, it is not possible to validly classify any of the events as coincidence events and the data must be discarded. Excessively protracted measurement time or tracer dose may also become necessary if count rate is too low owing to pulse pile-up.

Furthermore, owing to the design of the detector units of a PET machine, pulse pile-up events can lead to the mis-assignment of the position of detection within the detector crystal. The specific position of the radiation/detector interaction can be determined using a position sensitive photo-multiplier tube (PMT) and 'Anger' logic based on the output of the four anodes of the PMT. When a pile-up event occurs, the weighting of the radiation event within the crystal array is incorrect, so an interaction that occurred in one crystal block may be miss-assigned to a neighboring crystal in the detector block.

SUMMARY OF THE INVENTION

According to a first aspect of the invention, therefore, there is provided a imaging method, comprising:

collecting detector output data from a radiation detector positioned near a subject provided with a radio-active tracer; and resolving individual signals in the detector output data by (i) determining a signal form (or an impulse response) of signals present in said data, (ii) making parameter estimates of one or more parameters of said signals, wherein said one or more parameters comprise at least a signal temporal position, and (iii) determining the energy of each of said signals from at least said signal form and said parameter estimates;

whereby acceptable subject to detector distance is reduced or increased, spatial resolution is improved, tracer dose or concentration is reduced, subject radiation exposure is reduced and/or scanning time is reduced.

For example, in SPECT, typical tracer dose (using Tc99m) range from 400 MBq to 1200 MBq depending on the ligand; Tl201 doses are generally up to 4 MCi (that is, approximately 150 to 160 MBq); I-131 doses (diagnostic) are in the order of 20 to 40 MBq (that is, about 1 to 2 MCi). SPECT and planar imaging generally use the same dose. What limits the dose and/or image time is radiation exposure to the subject. Image quality is, therefore, generally count poor. Planar imaging acquisition times of 6 to 10 minutes are common; SPECT times (assuming the patient is comfortable) range from 10 to 30 minutes. Whole body planar sweeps are similar. Typical approaches for reducing acquisition time (or improving total number of counts) is by using multiple 'heads' in the gamma-ray detector (or 'camera'), but there are only a few three-head gamma cameras on the market; most are dual head and some are single head.

According to the present invention, therefore, a greater amount of usable data should be extractable from any particular (typical) measurement arrangement, thereby improving resolution or image quality without increasing subject radiation exposure or requiring additional gamma-ray detectors. Alternatively, subject radiation exposure could be reduced without loss of resolution or image quality. Tests thus far suggest that it is not unrealistic to expect in some applications to obtain a 5% to 30% reduction in the scanning time or dose and, in many applications, a reduction in scanning time or dose in the range 15% to 30%. In certain cases a reduction in scanning time or dose in the range 20% to 30% (and in other cases more) should be achievable.

The resolving of individual signals may comprise:
obtaining the detector output data as digitized detector output data in a form of a digital time series; and forming a mathematical model based on the digital time series and as a function of at least the signal form, the temporal position of the signals, and the amplitude of the signals;

wherein determining the energy of each of the signals comprises determining the amplitude of the signals based on the mathematical model, the amplitude being indicative of a radiation event.

The method may include gating the detector output data according to the output of another radiation detector, such as in a coincidence mode.

The method may comprise a medical imaging method, such as tomography. In one such embodiment, the method comprises performing PET tomography.

The use of the resolving of individual signals reduces scanning time per image or projection by 25% or more. In certain embodiment, use of the resolving of individual signals reduces scanning time per image or projection by 35% or more.

in PET, 5 to 8 mCi of F18 FDG, or more, are typically used. Scanning times are variable and depend on the detectors, gantry geometry, length of the Z-axis and injected dose. Better scanning times (at any single position of the subject) are presently 2 to 3 minutes (or marginally less). A typical PET detector ring Z depth is 25 cm, with—for example—5 cm overlap from one position to the next position. Thus, a whole body (base of skull to bottom of pelvis) scan usually comprises 6 or 7 positions. Overall emission phase times have dropped from 30 to 40 minutes for smaller dose older BGO 2-D scanners to 10 minutes for higher dose, newer 3-D LSO scanners. Transmission phase is comparable. In practice, it takes longer to set up and plan a scan than it does to acquire; for example, the radiation-on acquisition run is only one breathhold for chest, and one for abdomen and pelvis.

Thus, with PET it is again expected that the present invention will permit a greater amount of usable data to be extractable from any particular (typical) measurement arrangement, thereby improving resolution or image quality without increasing subject radiation exposure or requiring additional gamma-ray detectors, reducing exposure without loss of resolution or image quality, or reducing scanning time or dose.

In other embodiments, the method is an X-ray transmission imaging method or a CT imaging method.

In one embodiment, use of the resolving of individual signals (described above) reduces scanning time per projection by at least 35%, and in another embodiment by more than 35%.

Thus, this method endeavors to characterize as much data as possible, but it will be appreciated that it may not be possible to adequately characterize some data (which hence is termed 'corrupt data'), as is described below. It will be understood that the term 'signal' is interchangeable in this context with 'pulse', as it refers to the output corresponding to individual detection events rather than the overall output signal comprising the sum of individual signals. It will also be appreciated that the temporal position (or timing) of a signal can be measured or expressed in various ways, such as according to the time (or position in the time axis) of the maximum of the signal or the leading edge of the signal. Typically this is described as the arrival time ('time of arrival') or detection time.

It will also be understood that the term 'detector data' refers to data that has originated from a detector, whether processed subsequently by associated or other electronics within or outside the detector.

The method may include constructing a model of the data from the parameter estimates, and determining the accuracy of the parameter estimates based on a comparison between the detector output data and the model.

The signal form (or impulse response) may be determined by a calibration process that involves measuring the detector's time domain response to one or more single event detections to derive from that data the signal form or impulse response. A functional form of this signal form may then be obtained by interpolating the data with (or fitting to the data) a suitable function such as a polynomial, exponential or spline. A filter (such as an inverse filter) may then be constructed from this detector signal form. An initial estimate of signal parameters may be made by convolution of the output data from the detector with the filter. Signal parameters of particular interest include the number of signals and the temporal position (or time of arrival) of each of the signals.

The particular signal parameters of interest can then be further refined. Firstly, the estimate of the number and arrival times of signals is refined with the application of peak detection and a threshold. Secondly, knowledge of the number of signals and their arrival time, coupled with the detector impulse response (and hence signal form) makes it possible to solve for the energy parameters of the signals.

The accuracy of the parameter estimation can be determined or 'validated' by comparing a model (in effect, an estimate) of the detector data stream (constructed from the signal parameters and knowledge of the detector impulse response) and the actual detector output. Should this validation process determine that some parameters are insufficiently accurate, these parameters, are discarded. In spectroscopic analysis using this method, the energy parameters deemed sufficiently accurate may be represented as a histogram.

The method may include making the estimates of signal parameters in accordance with the signal form (i.e. the impulse response of the detector used for generating the signal). The method may include determining the signal form by a calibration process including measuring the response of the detector to one or more single detections to derive a data based model of the signal form. In particular, the method may include obtaining a functional form of the model by interpolating the data with a function to generate the expected signal form. The function may be a polynomial, exponential or spline function.

The method may include designing a filter on the basis of the predetermined form of the individual signals produced by the radiation detector. The filter may be, for example, of matched fitter or inverse filter form.

In one embodiment, the method includes using convolution of the detector output and filter to make an initial estimate of the signal parameters. The method may include refining the estimate of the signal parameters. The method may include refining the estimate of signal number with a peak detection process. The method may include making or refining the estimate of signal temporal position by application of a peak detection process. The method may include refining the estimate of signal energy by solving a system of linear equations, by matrix inversion or by iterative techniques.

In an embodiment of the invention, the method includes creating a model of the detector output using the signal parameters in combination with the detector impulse response. The method may include performing error detection by, for example, comparing the actual detector output data with the model of the detector output, such as by using least-squares or some other measure of the difference between the data and the model.

The method may include discarding parameters deemed not sufficiently accurately estimated.

In one embodiment, the method includes presenting all sufficiently accurate energy parameters in a histogram.

The data may include signals of different forms. In this case, the method may include determining where possible the signal form of each of the signals.

In one embodiment, the method includes progressively subtracting from the data those signals that acceptably conform to successive signal forms of a plurality of signal forms, and rejecting those signals that do not acceptably conform to any of the plurality of signal forms.

In one embodiment, the method is characterized by data throughput of greater than 90% for an input count rate of 50 kHz.

In one embodiment, the method is characterized by data throughput of greater than 90% for input count rates between 25 and 250 kHz.

In one embodiment, the method is characterized by data throughput of greater than 95% for an input count rate of 25 kHz.

In one embodiment, the method is characterized by data throughput of greater than 95% for input count rates between 25 and 100 kHz.

In one embodiment, the method is characterized by data throughput of greater than 80% for an input count rate of 250 kHz.

In one embodiment, the method is characterized by data throughput of greater than 50% for input count rates between 250 and 2500 kHz.

In one embodiment, the method comprises using a SPECT camera and a scan time per projection or image of no more than 15 s.

In one embodiment, the method comprises using a SPECT camera and a scan time per projection or image of no more than 13 s.

Comparable performance may advantageously be provided according to imaging method.

In a second aspect, the invention provides an imaging apparatus, comprising:
- a radiation detector locatable near a subject provided with a radio-active tracer, for detecting radiation emitted by the tracer, and for outputting detector data in response thereto; and
- a processor for receiving the detector data in digitized form, and programmed to determine the signal form of each of the signals present in the data, to make parameter estimates of one or more parameters of the signals, and to determine the energy of each of the signals from at least the signal form and the parameter estimates, wherein the one or more parameters comprise at least a signal temporal position;
- whereby acceptable subject to detector distance is reduced or increased, spatial resolution is improved, tracer dose or concentration is reduced, subject radiation exposure is reduced and/or scanning time is reduced.

The processor may be programmed to obtain the detector output data in a form of a digital time series and to form a mathematical model based on the digital time series and as a function of at least the signal form, the temporal position of the signals, and the amplitude of the signals, wherein determining the energy of each of the signals comprises determining the amplitude of the signals based on the mathematical model, the amplitude being indicative of a radiation event.

The apparatus may include a plurality of comparable radiation detectors and the apparatus may be configured to gate the detector data of any one or more of the detectors according to the detector data of any one or more other of the detectors, such as in a coincidence mode.

The apparatus may be a medical imaging apparatus, such as a tomography apparatus. In one such embodiment, the apparatus comprises a PET apparatus.

In one embodiment, the apparatus is characterized by data throughput of greater than 90% for an input count rate of 50 kHz.

In one embodiment, the apparatus is characterized by data throughput of greater than 90% for input count rates between 25 and 250 kHz.

In one embodiment, the apparatus is characterized by data throughput of greater than 95% for an input count rate of 25 kHz.

In one embodiment, the apparatus is characterized by data throughput of greater than 95% for input count rates between 25 and 100 kHz.

In one embodiment, the apparatus is characterized by data throughput of greater than 80% for an input count rate of 250 kHz.

In one embodiment, the apparatus is characterized by data throughput of greater than 50% for input count rates between 250 and 2500 kHz.

According to a third aspect of the invention, there is provided an imaging method, comprising:
- collecting detector output data from a radiation detector positioned near a subject provided with a radio-active tracer; and
- resolving individual signals in the detector output data by (i) obtaining or expressing the detector output data as a digital series (such as a digital time series or a digitized spectrum), (ii) obtaining or determining a signal form (or equivalently the impulse response) of signals present in the data, (iii) forming a transformed signal form by transforming the signal form according to a mathematical transform, (iv) forming a transformed series by transforming the digital series according to the mathematical transform, said transformed series comprising transformed signals, (v) evaluating a function of at least the transformed series and the transformed signal form (and optionally of at least one parameter of the transformed signals) and thereby providing a function output, (vi) modelling the function output according to a model (such as by modelling the function output as a plurality of sinusoids), (vii) determining at least one parameter of the function output based on the model, and (viii) determining a parameter of the signals from the at least one determined parameter of the function output;
- whereby acceptable subject to detector distance is reduced or increased, spatial resolution is improved, tracer dose or concentration is reduced, subject radiation exposure is reduced and/or scanning time is reduced.

The signal form may generally be regarded as characterising the interaction between the detector and the radiation (or other detected input) that was or is being used to collect the data. It may be determined or, if known from earlier measurements, calibrations or the like, obtained from (for example) a database.

In some embodiments, transforming the digital series according to the mathematical transform comprises forming a model of the digital series and transforming the model of the digital series according to the mathematical transform.

In certain embodiments, the method includes determining a plurality of parameters of the transformed signals, such as frequency and amplitude.

In certain particular embodiments, the transform is a Fourier transform, such as a fast fourier transform or a discrete fourier transform, or a wavelet transform. Indeed, in certain embodiments the transform may be applied somewhat differently to the signal form and digital series respectively. For example, in one embodiment the mathematical transform is the Fourier transform, but the signal form is transformed with a discrete fourier transform and the digital series is transformed with a fast fourier transform.

In one embodiment, the transform is a Fourier transform and the function is representable as $$Y(k)=X(k)/H(k)$$

where $X(k)$ is the transformed series and $H(k)$ is the transformed signal form.

Thus, the method of this aspect endeavours to determine a parameter of the signals and hence of as much of the data as possible, but it will be appreciated that it may not be possible to do so for some data (which hence is termed 'corrupt data'), as is described below. It will be understood that the term 'signal' is interchangeable in this context with 'pulse', as it refers to the output corresponding to individual detection events rather than the overall output signal comprising the sum of individual signals. It will also be appreciated that the temporal position (or timing) of a signal can be measured or expressed in various ways, such as according to the time (or position in the time axis) of the maximum of the signal or the leading edge of the signal. Typically this is described as the arrival time ('time of arrival') or detection time.

It will also be understood that the term 'detector data' refers to data that has originated from a detector, whether processed subsequently by associated or other electronics within or outside the detector.

The signal form (or impulse response) may be determined by a calibration process that involves measuring the detector's impulse response (such as time domain response or frequency domain response) to one or more single event detections to derive from that data the signal form or impulse response. A functional form of this signal form may then be obtained by interpolating the data with (or fitting to the data) a suitable function such as a polynomial, exponential or spline. A filter (such as an inverse filter) may then be constructed from this detector signal form. An initial estimate of signal parameters may be made by convolution of the output data from the detector with the filter. Signal parameters of particular interest include the number of signals, the temporal position (or time of arrival) of each of the signals and the energy of the signals.

The particular signal parameters of interest can then be further refined.

The accuracy of the parameter estimation can be determined or 'validated' by comparing a model of the detector data stream (constructed from the signal parameters and knowledge of the detector impulse response) and the actual detector output. Should this validation process determine that some parameters are insufficiently accurate, these parameters are discarded. In spectroscopic analysis using this method, the energy parameters deemed sufficiently accurate may be represented as a histogram.

The detector output data may include signals of different forms. In this case, the method may include determining where possible the signal form of each of the signals.

In one embodiment, the method includes progressively subtracting from the data those signals that acceptably conform to successive signal forms of a plurality of signal forms, and rejecting those signals that do not acceptably conform to any of the plurality of signal forms.

In a fourth aspect, the invention provides an imaging apparatus, comprising:
  a radiation detector locatable near a subject provided with a radio-active tracer, for detecting radiation emitted by the tracer, and for outputting detector data in response thereto; and
  a processor for receiving the data as a digital series, and programmed to (i) obtain or determine a signal form (or equivalently the impulse response) of signals present in the data, (ii) form a transformed signal form by transforming the signal form according to a mathematical transform, (iii) form a transformed series by transforming the digital series according to the mathematical transform, said transformed series comprising transformed signals, (iv) evaluate a function of at least the transformed series and the transformed signal form (and optionally of at least one parameter of the transformed signals) and thereby provide a function output, (v) model the function output according to a model (such as by modelling the function output as a plurality of sinusoids), (vi) determine at least one parameter of the function output based on the model, and (vii) determine a parameter of the signals from the at least one determined parameter of the function output;
  whereby acceptable subject to detector distance is reduced or increased, spatial resolution is improved, tracer dose or concentration is reduced, subject radiation exposure is reduced and/or scanning time is reduced.

The apparatus may include an analog to digital converter adapted to receive the data, to convert the data into digitized form, and forward the data in digitized form to the processor. This would be of particular use where the detector outputs analog data.

The processor may comprise a field programmable gate array (or an array thereof). Alternatively, the processor may comprise a digital signal processor (or an array thereof). In a further alternative, the processor comprises a field programmable gate array (or an array thereof) and a digital signal processor (or an array thereof). In still another embodiment, the processor comprises an ASIC (Application Specific Integrated Circuit). The apparatus may include an analog front end that includes the analog to digital converter.

The apparatus may include an electronic computing device in data communication with the processor, for controlling the processor and for displaying an output of the processor.

According to another aspect of the invention, there is provided an imaging method, comprising:
  collecting detector output data from a radiation detector positioned near a subject provided with a radio-active tracer; and
  resolving individual signals in the detector output data by (i) obtaining or expressing the detector output data as a digital series, (ii) obtaining or determining a signal form (or equivalently the impulse response) of signals present in the data, (iii) forming a transformed signal form by transforming the signal form according to a mathematical transform, (iv) forming a transformed series by transforming the digital series according to the mathematical transform, said transformed series comprising transformed signals, (v) evaluating a function of at least the transformed series and the transformed signal form (and optionally of at least one parameter of the transformed signals) and thereby providing a function output, (vi) modelling the function output according to a model (such as by modelling the function output as a plurality of sinusoids), (vii) determining at least one parameter of the function output based on the model, and (viii) determining a parameter of the signals from the at least one determined parameter of the function output;
  whereby acceptable subject to detector distance is reduced or increased, spatial resolution is improved, tracer dose or concentration is reduced, subject radiation exposure is reduced and/or scanning time is reduced.

It should be noted that the various optional features of each aspect of the invention may be employed where suitable and desired with any of the other aspects of the invention.

BRIEF DESCRIPTION OF THE DRAWINGS

In order that the invention may be more clearly ascertained, preferred embodiments will now be described, by way of example only, with reference to the accompanying drawing, in which:

FIG. 2b is a schematic view of a detector unit of the detector module of FIG. 2a;

DETAILED DESCRIPTION OF THE EMBODIMENTS

Figure 1:
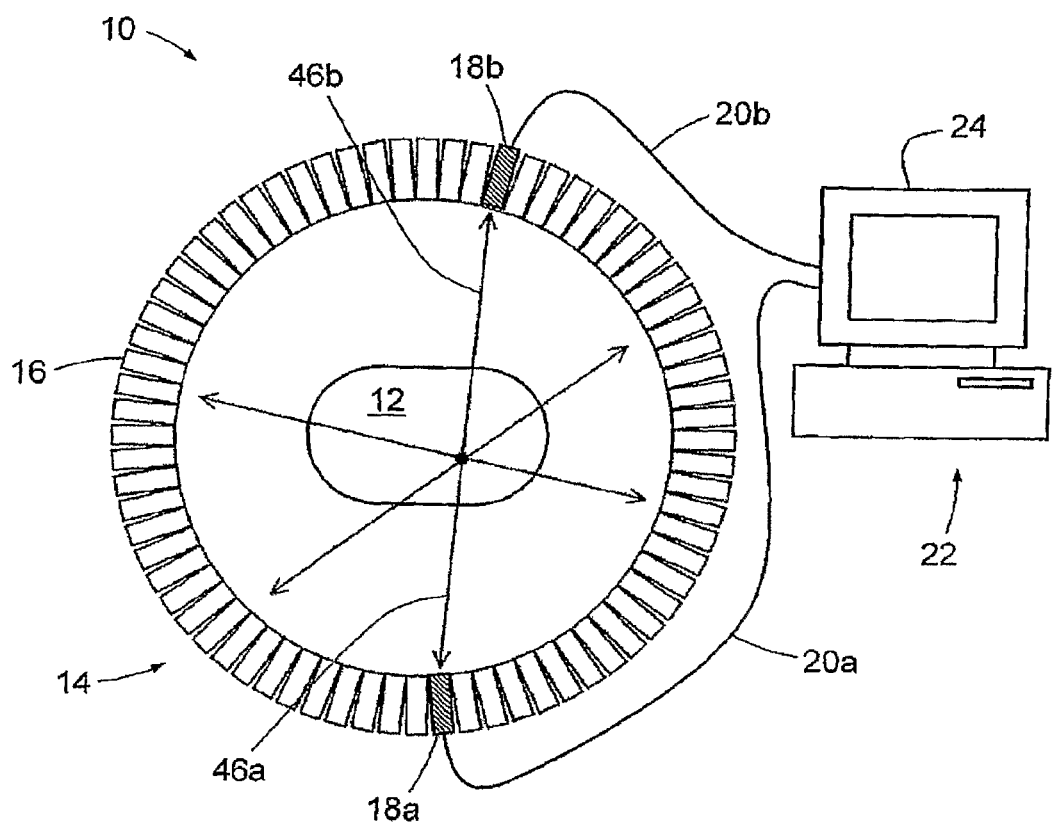
FIG. 1 is a schematic view of a PET apparatus according to an embodiment of the present invention.

FIG. 1 is a schematic view of a PET apparatus 10 according to an embodiment of the present invention, shown with a subject to be imaged 12. Apparatus 10 includes a detector ring 14 comprising a plurality of detector Modules 16 (including exemplary detector modules 18a,18b), data cables (including exemplary data cables 20a,20b corresponding to detector modules 18a,18b) for receiving the output of detector modules 16. Apparatus 10 also includes a data capture and analysis module 22 configured to receive data from the data cables and perform the data analysis described below.

It should be appreciated that data capture and analysis module 22 may comprise either a computing device configured to both collect data and analyze that data as described below, or a plurality of components such as a data collection device and a distinct data analysis device for performing these functions. In the latter case, such data collection and data analysis devices may each comprise computing devices. In both cases, data capture and analysis module 22 includes a display. In the present embodiment, data capture and analysis module 22 comprises a computer with a display 24.

Data capture and analysis module 22 includes a signal processing unit that comprises two parts: 1) an analog to digital converter which produces a digital output corresponding to the analog output of the detector unit, and 2) a processing unit which implements digital signal processing (DSP) routines in accordance with the present invention.

Figure 2A:
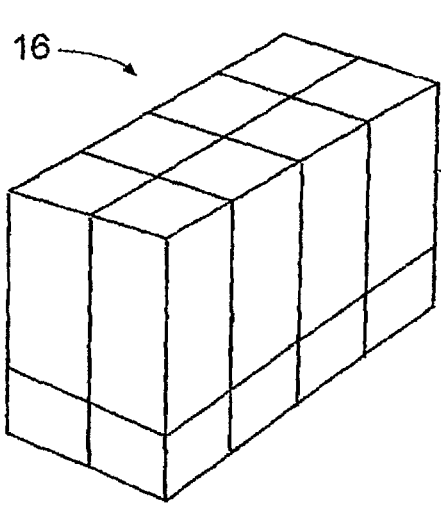
FIG. 2a is a schematic view of a detector module of the apparatus of FIG. 1.
Figure 2B:
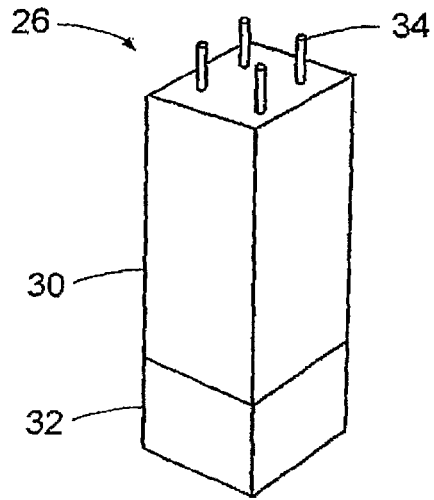

FIG. 2a is a schematic view of detector module 16, with radiation-sensitive face directed downwards in this view. Detector module 16 comprises a group of eight detector units 26, an example of which is shown schematically in FIG. 2b. Detector unit 26 comprises a crystal block 30 coupled to a photomultiplier tube (PMT) assembly 32; PMT assembly 32 has four anodes 34 at which output signals can be collected.

Figure 2C:
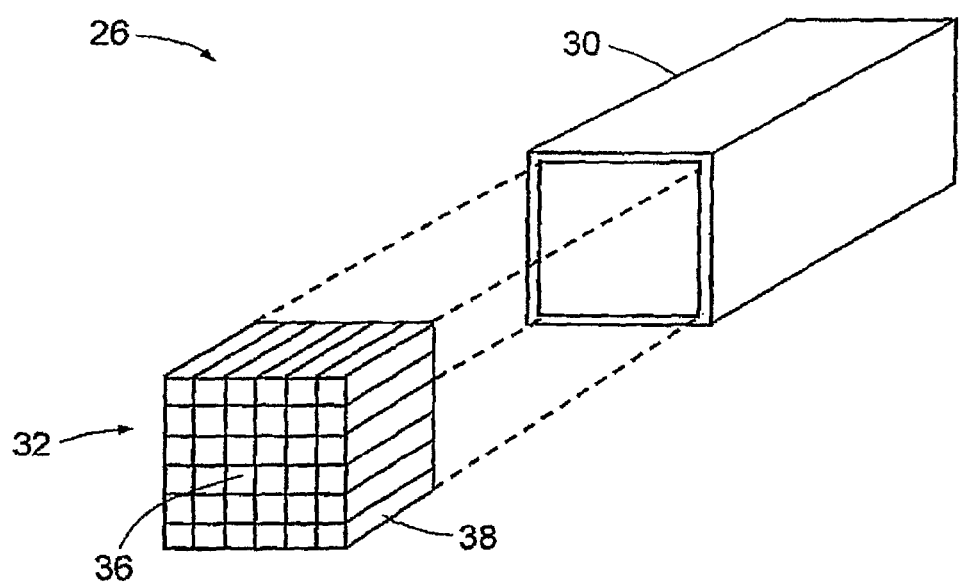
FIG. 2c is a partially exploded schematic view of the detector unit of FIG. 2b.

FIG. 2c is a partially exploded schematic view of detector unit 26, in which is shown crystal block 30 and PMT 32. Crystal block 30 has a forward face 36 of 38×38 mm, and a depth of 30 mm; crystal block 30 comprises a 6×6 grid of individual BGO crystals 38.

Figure 2D:
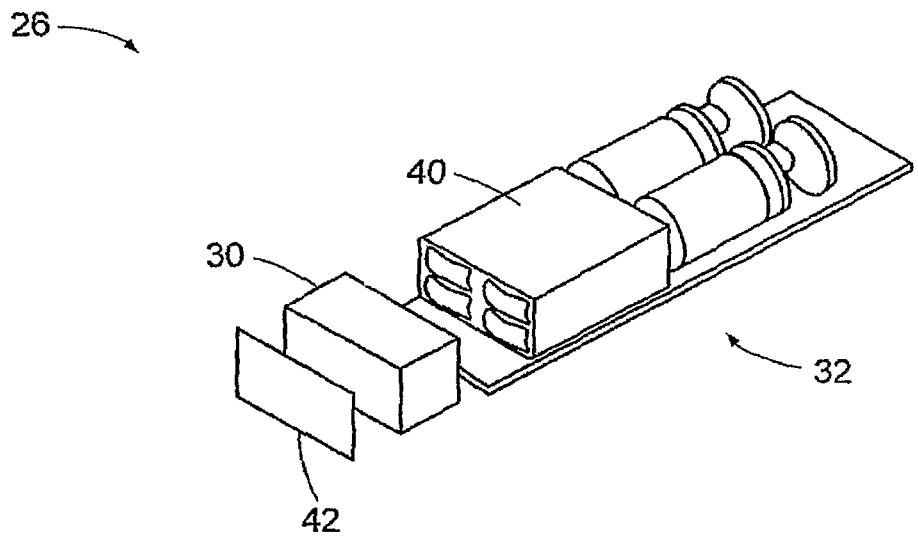
FIG. 2d is a more detailed schematic view of the detector unit of FIG. 2b.

FIG. 2d is a more detailed exploded view of detector unit 26, including crystal block 30 and PMT assembly 32. PMT assembly 32 includes two PMTs 40. Forward face 36 and sides of crystal block 30 are covered with light sealing tape 42, and forward face 36 is additionally shielded by a thin plastic sealing protective sheet 44.

PET apparatus 10 operates, as explained above, as a coincidence detector. Referring to FIG. 1, when a gamma-ray 46a is detected by, for example, detector module 18a, apparatus 10 only registers that detection as an event of interest if another gamma-ray 46b is detected at the same time (to within some predefined Δt) by another detector module that is opposite that part of the subject being imaged, in this example detector module 18b. In addition, both gamma-rays must arise from electron/positron annihilation events, so each have an energy of 511 keV±ΔE, where ΔE is typically 10% or ~50 keV. Resolution is optimized and background minimized if both Δt and ΔE are minimized, but doing so reduces count rate. Hence, it is important to extract as much usable data from the output of the detector modules 16, and hence to minimize pulse pile-up. The technique employed by data capture and analysis module 22 of apparatus 10 to reduce the effects of pulse pile-up is described below. It is envisaged, however, that a substantial reduction in corrupt data due to pulse pile-up is achievable, such that either or both Δt and ΔE can be reduced (in the former case with the improved time-stamping provided by the present invention) without signcant loss of resolution or increase in background. In addition, it is envisaged that the reduction in corrupt data due to pulse pile-up may permit reduced scanning times or reduced radioactive tracer dose, as the same usable data will be extractable from less input data.

Furthermore, the present invention is expected to allow detector ring 14 to be smaller in diameter (as apparatus 10 can accommodate higher count rates without substantial loss of usable data) or greater in diameter (as apparatus 10 rejects fewer events owing to pulse-pile up, so still collect sufficient events even with greater source to detector distances).

Comparable benefits are also expected in non-coincidence applications of the technique of the present invention, such as SPECT.

When a gamma-ray is emitted within detector ring 14 and is incident on one of detector modules 16, it passes into a detector unit 26 and its energy is transferred from the gamma-ray to electrons within a crystal 38. Upon the emission of ultra-violet photons the electrons lose this energy, promoting electrons within the crystal to excited states. Upon the emission of ultra-violet photons the electrons decay to lower energy states. The aforementioned ultra-violet photons pass through the optical window to the photocathode of a PMT 40 where they are converted into photoelectrons and subsequently multiplied by an electron multiplier before arriving at an anode 34 of the PMT 40. A further multiplication stage may be provided by an on-board pre-amplifier. In this manner an electrical signal, whose amplitude is proportional to the energy of the incident gamma-rays, is present at the detector output terminals of detector module 16. It will also be appreciated that the detector may additionally include a mu metal magnetic shield located about the sides of PMT assembly 32 and extending forwardly of the PMT assembly 32 sufficiently far to surround a portion of the BGO crystals 38.

Scintillation detectors of this kind have high efficiencies, that is, exhibit a high probability of detecting an incident gamma-ray. However, they also exhibit a relatively long detector response time. The detector response time is the time required by the detector to detect an incident gamma-ray and return to a state where the next incident gamma-ray can be accurately detected. Radiation detectors with long detector response times are thus prone to pulse pile-up. That is, the output, which ideally consists of completely discrete pulses each corresponding to the incidence of a single gamma-ray, instead exhibits a waveform in which individual pulses can overlap making them difficult to characterize.

Figure 3A:
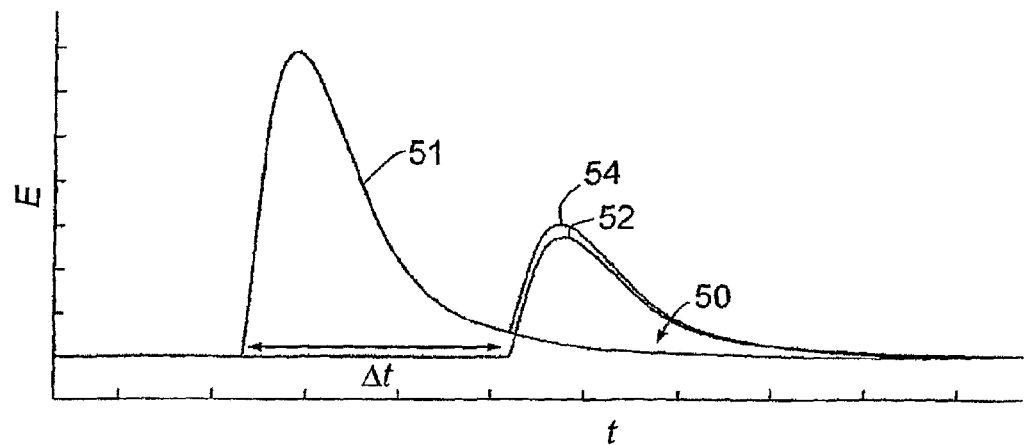
FIGS. 3a, 3b and 3c are graphs illustrating pulse pile-up.
Figure 3B:
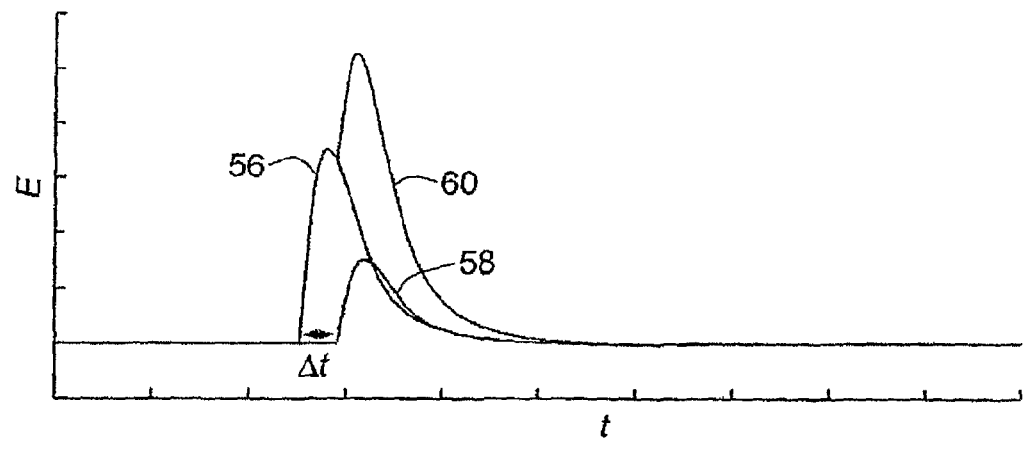
Figure 3C:
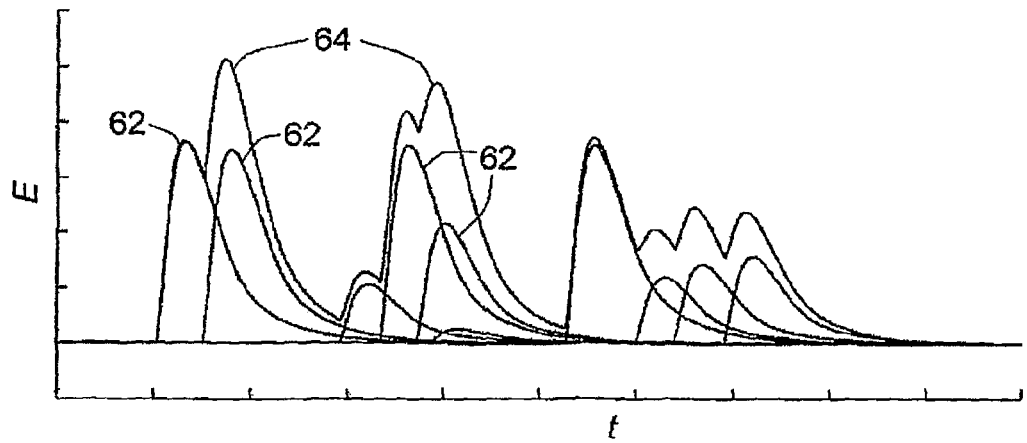

FIGS. 3a, 3b and 3c illustrate the effect of pulse pile-up, and show illustrative signals or pulses plotted as energy E versus time t (both in arbitrary units). FIG. 3a illustrates so-called 'tail-end pile-up' where, depending on the type of pulse conditioning employed, the tail 50 of one pulse 51 can provide a significant positive or negative bias positive in the illustrated example to the amplitude of a subsequent pulse 52. Although the time displacement between the two pulses, Δt, is relatively large when compared with the overall time interval for which the pulses prevail, the signal envelope or resultant waveform 54 is significantly above zero at the arrival of the second pulse 52.

The absence of a true zero signal state between the two pulses corrupts the pulse characterization, as the amplitude of the second pulse is falsely inflated by the tail of the first. FIG. 3b illustrates another form of pulse pile-up, 'peak pile-up'. Here two pulses 56 and 58 arrive closely spaced in time i.e. the time displacement Δt between the pulses is small compared with the overall time interval over which the pulses prevail. The resultant output waveform 60 appears more or less as a single pulse of somewhat greater amplitude than either of the component pulses. In situations where the flux of gamma-rays through the detector is extreme, it is not uncommon to have multiple events arriving within the response time of the detector leading to multiple pile-up events. Such a case is illustrated by FIG. 3c. Multiple signals or pulses (such as those shown at 62) arrive with random time separation Δt and sum to produce a resultant waveform 64 from which the parameters of the component signals are difficult to extract.

One component of the method of addressing pulse pile-up according to this embodiment is the estimation of certain parameters of the signals or pulses; these parameters are the number, time-of-arrival and energy of all gamma-rays in the detector data stream. These parameters are estimated, according to this embodiment, by modeling the signals in the data stream mathematically. The model employed in this embodiment includes certain assumptions about the data and the apparatus, as are discussed below.

Figure 4:
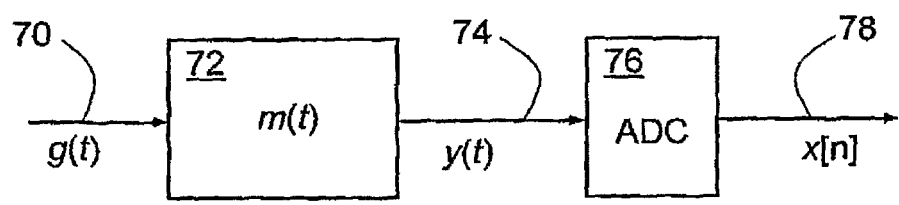
FIG. 4 is a diagram illustrating the mathematical modeling of radiation detection used by the signal processing method embodied in the apparatus of FIG. 1.

FIG. 4 is a diagram that illustrates the modeling of the radiation detection process. The radiation g(t) 70 is incident on the detector 72 represented by the measurement process m(t), resulting in output data from the detector y(t) 74. The addition of a sampling process 76 produces the digital detector data or 'time-series' x[n] 78.

Figure 5:
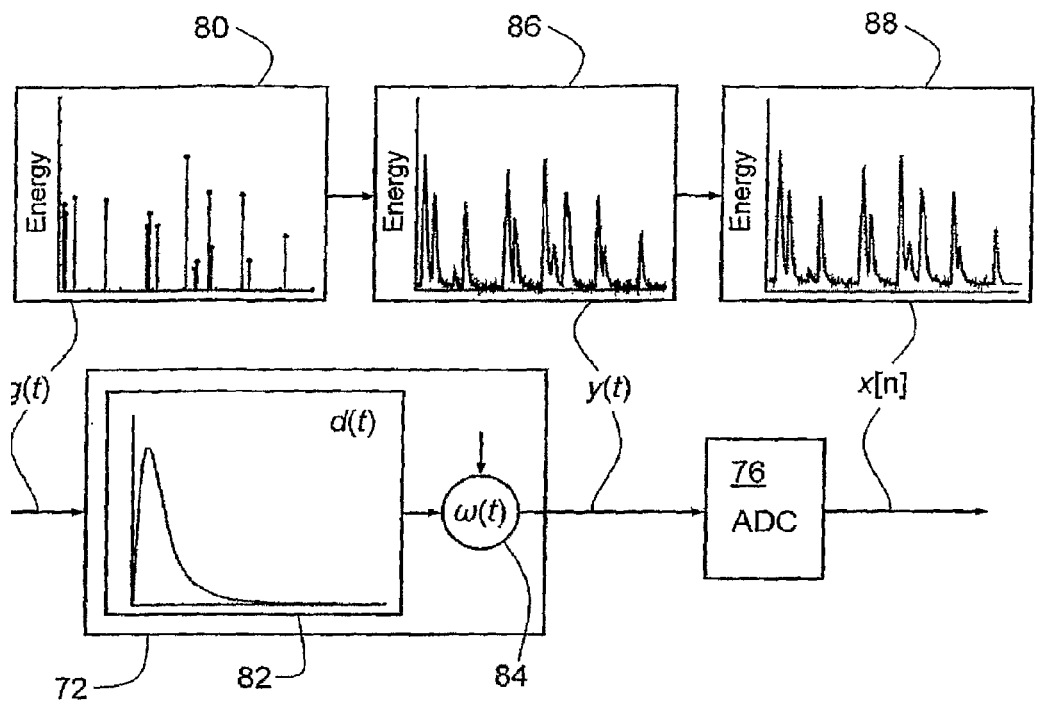
FIG. 5 is a diagram detailing the mathematical model of radiation detection used by the signal processing method embodied in the apparatus of FIG. 1.

It is possible to add to the above-described model some knowledge about the physical processes of radiation detection. FIG. 5 illustrates a more detailed mathematical model of the detection process shown in FIG. 4. The input g(t) to the detector is characterized by Equation 1, in which the input g(t) is assumed to be an unknown number (N) of delta-function-like impulses of random amplitude (α) and time of arrival (τ). An illustrative example of such input is shown at 80.

$$g(t) = \sum_{i=1}^{N} \alpha_i \delta(t - \tau_i) \tag{1}$$

$$i = 1, 2, 3, \ldots, N.$$

The radiation detector is assumed to have a specific response to the incoming radiation, referred to as the detector impulse response d(t) (or, equivalently, the signal form of the signals in the data), which is illustrated at 82. The digitized version of the detector impulse response (i.e. signal form) is denoted d[n].

The output from the detector is shown at 86 and characterized by Equation 2, in which the detector output y(t) is the sum of an unknown number of signals of predetermined signal form d(t), with unknown energy (α) and unknown time of arrival (τ). Sources of random noise ω(t) 84 are also considered. The digital detector data x[n] 88 is produced by the analog to digital converter 76.

$$y(t) = \sum_{i=1}^{N} \alpha_i d(t - \tau_i) + \omega(t) \quad (2)$$

$$i = 1, 2, 3, \ldots, N.$$

The digitized signal x[n] (which constitutes a time series of data) at the output of the analog to digital converter 76, as illustrated at 88; is therefore given by $$x[n] = \sum_{i=1}^{N} \alpha_i d[n - \Delta_i] + \omega[n], \quad (3)$$

where d[n] is the discrete time form of the signal form d(t), $\Delta_i$ is the delay in samples to the ith signal, and ω[n] is the discrete time form of the noise. The digitized signal x[n] may also be written in matrix form as $$x = A\alpha + \omega \quad (4)$$

where A is an M×N matrix, the entries of which are given by $$A(n, i) = \begin{cases} d[n - \Delta_i] & \Delta_i \leq n < \min(M, \Delta_i + T - 1) \\ 0 & \text{otherwise.} \end{cases} \quad (5)$$

Also, T is the length of d[n] in samples, M is the total number of samples in the digitized signal x[n], α is the vector of N signal energies, and ω is the noise vector of length M. Matrix A may also be depicted as follows:

$$A = \begin{bmatrix} 0 & 0 & \cdots & 0 \\ \vdots & & & \\ 0 & \vdots & & \\ d[1] & & & \vdots \\ d[2] & 0 & & \\ \vdots & d[1] & & \\ d[T] & & & \\ 0 & \vdots & \ddots & 0 \\ & & & d[1] \\ \vdots & d[T] & & d[2] \\ & & & \vdots \\ 0 & \cdots & 0 & d[r < T] \end{bmatrix} \begin{matrix} \\ \\ \\ \leftarrow \text{row } \Delta_1 \\ \\ \leftarrow \text{row } \Delta_2 \\ \\ \\ \leftarrow \text{row } \Delta_N \\ \\ \\ \end{matrix}$$

Thus, the columns of matrix A contain multiple versions of the signal form. For each of the individual columns the starting point of the signal form is defined by the signal temporal position. For example, if the signals in the data arrive at positions 2, 40, 78 and 125, column 1 of matrix A will have '0' in the first row, the 1st datum point of the signal form in the second row, the 2nd datum point of the signal form in the 3rd row, etc. The second column will have '0' up to row 39 followed by the signal form. The third column will have '0' up to row 77; the fourth column will have '0' up to row 124 and then the signal form. Hence the size of matrix A is determined by the number of identified signals (which becomes the number of columns), while the number of rows depends on the number of samples in the time series.

The signal processing method of this embodiment thus endeavors to provide an accurate estimate of some unknown parameters of the detector data, including not only the number of component signals (N) in the detector output but also the energy (α) and time-of-arrival (τ) of each of the component signals.

Signal Processing Method

Figure 6:
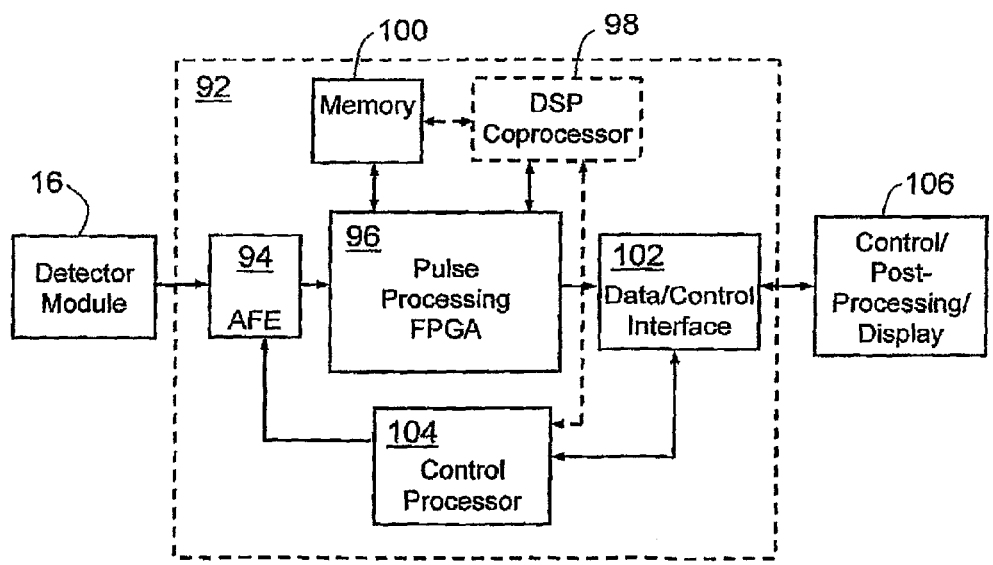
FIG. 6 is a schematic diagram of the functional elements of the data capture module of FIG. 1.

FIG. 6 is a schematic diagram of the functional elements of data capture and analysis module 22 of FIG. 1, with detector module 16, and is provided to explain in more detail the signal processing method for pulse pile-up recovery employed by the apparatus of FIG. 1. Referring to FIG. 6, detector module 16 is connected to a pulse processing board 92 via an analog front end (AFE 94). The purpose of the AFE 94 is to digitize the signal produced by detector module 16 by performing analog to digital conversion at, in this embodiment, 125 MHz with 12-bit conversion accuracy.

Figure 7A:
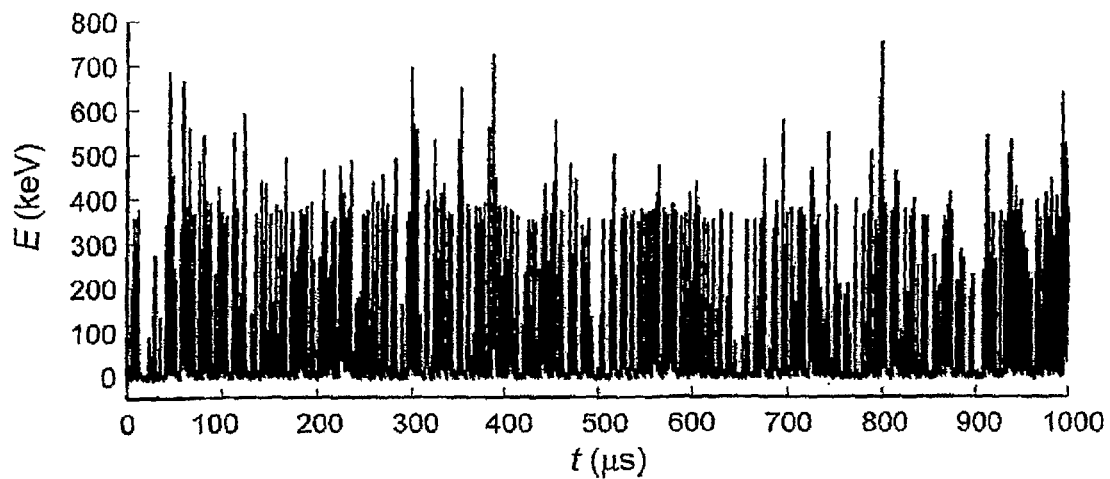
FIGS. 7a, 7b and 7c are plots of unprocessed digitized data collected directly from the output of the detector of FIG. 2 over time ranges of 1000 µs, 100 µs and 10 µs respectively.
Figure 7B:
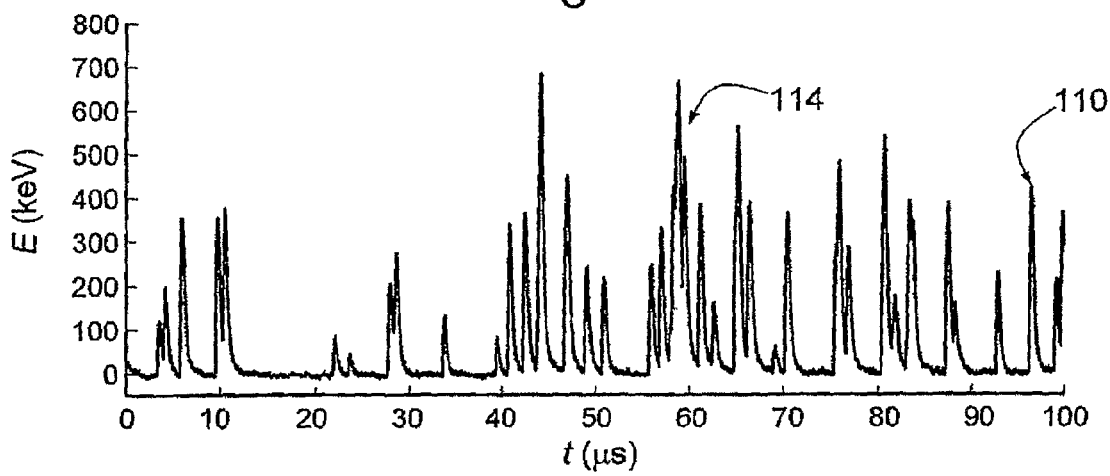
Figure 7C:
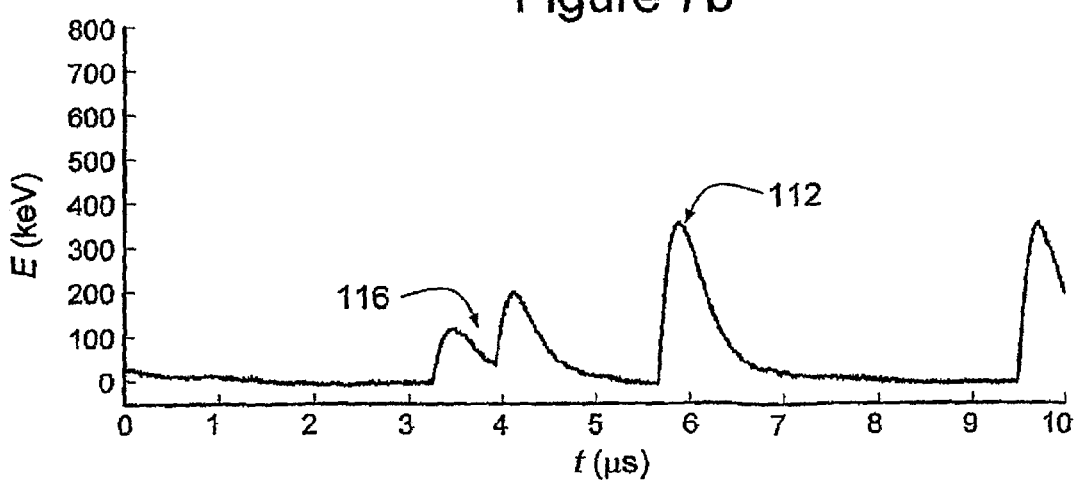

FIGS. 7a, 7b and 7c illustrate the waveform resulting from such digitization, over time ranges of 1000 microseconds, 100 microseconds and 10 microseconds respectively. The various peaks in these figures correspond to the detection of respective gamma-rays. Some peaks appear as discreet signals or pulses 110, 112 which may indicate the presence of only a single gamma-ray. Other peaks are due to the pile-up either of two peaks 116 or of three or more peaks 114.

After the output of detector module 16 has been digitized by AFE 94, the signal processing method for pulse pile-up recovery is implemented. Referring again to FIG. 6, the digital signal produced by AFE 94 is passed into the pulse processing Field Programmable Gate Array (FPGA) 96. The pulse processing FPGA (96) then implements the pulse processing method of this embodiment; a digital signal processing coprocessor 98 may optionally be used to assist the pulse processing FPGA 96 to implement the pulse processing method. Variables required by the pulse processing FPGA 96 and data produced at interim steps of the pulse processing method are optionally stored in memory 100. The signal processing is controlled via a Data/Control Interface 102 which, in conjunction with a Control Processor 104, can be used to modify the implementation of the signal processing. The output data from the signal processing method can be displayed on a display 106 via the Data/Control Interface 102. Display 106 is provided in a computer that may, if desired, be used to perform post-processing and system control.

Figure 8:
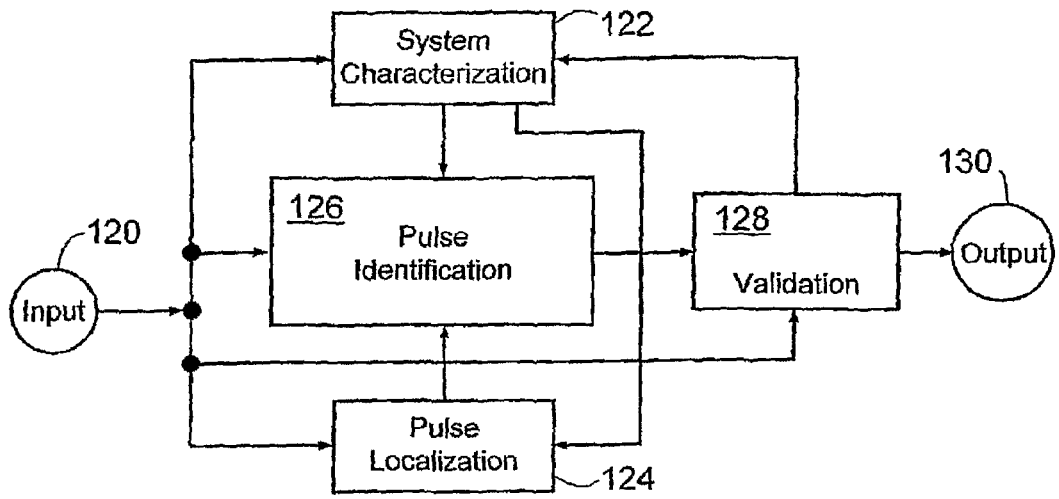
FIG. 8 is a schematic representation of the signal processing method for pulse pile-up recovery employed by the apparatus of FIG. 1 for analyzing spectroscopic data according to this embodiment of the invention.

FIG. 8 is a schematic diagram of the signal processing method for pulse pile-up recovery of radiation signals in the detector time series of this embodiment. The digitized detector signal (from AFE 94) forms the input 120 for this signal processing method. Offline System Characterization 122 is used to determine the detector impulse response unique to the particular digitized detector signal. Characterization data generated in System Characterization phase 122 is used in a Pulse Localization phase 124. The Pulse Localization phase 124 estimates, in real-time, the number and temporal position (or time-of-arrival) of radiation pulses within the digitized detector signal. In a Pulse Identification phase 126, the digitized detector signal, the detector impulse response and the output from the Pulse Localization phase 124 are used to determine the energy of the signals or pulses. Validation 128 involves comparing the output of the Pulse Identification phase 126 with the digitized detector signal 120. If this comparison indicates that any of the pulse parameters have been estimated inaccurately, those parameters are rejected so that only valid, data is output 130. The error signal generated in the Validation phase 128 is also employed in System Characterization 122. In circumstances where the detector impulse response may change over time, such as owing to the aging of components, temperature variations or increased radiation fluxes, System Characterization 122 updates the detector impulse response online and adaptively by employing the error signal. Such updating of the detector impulse response may be performed with any suitable adaptive method, such as least mean squares adaptation, normalized least mean squares adaptation or recursive least squares adaptation as described, for example, by S. Haykin [*Adaptive Filter Theory*, 4th Ed, Prentice Hall, 2002].

Figure 9:
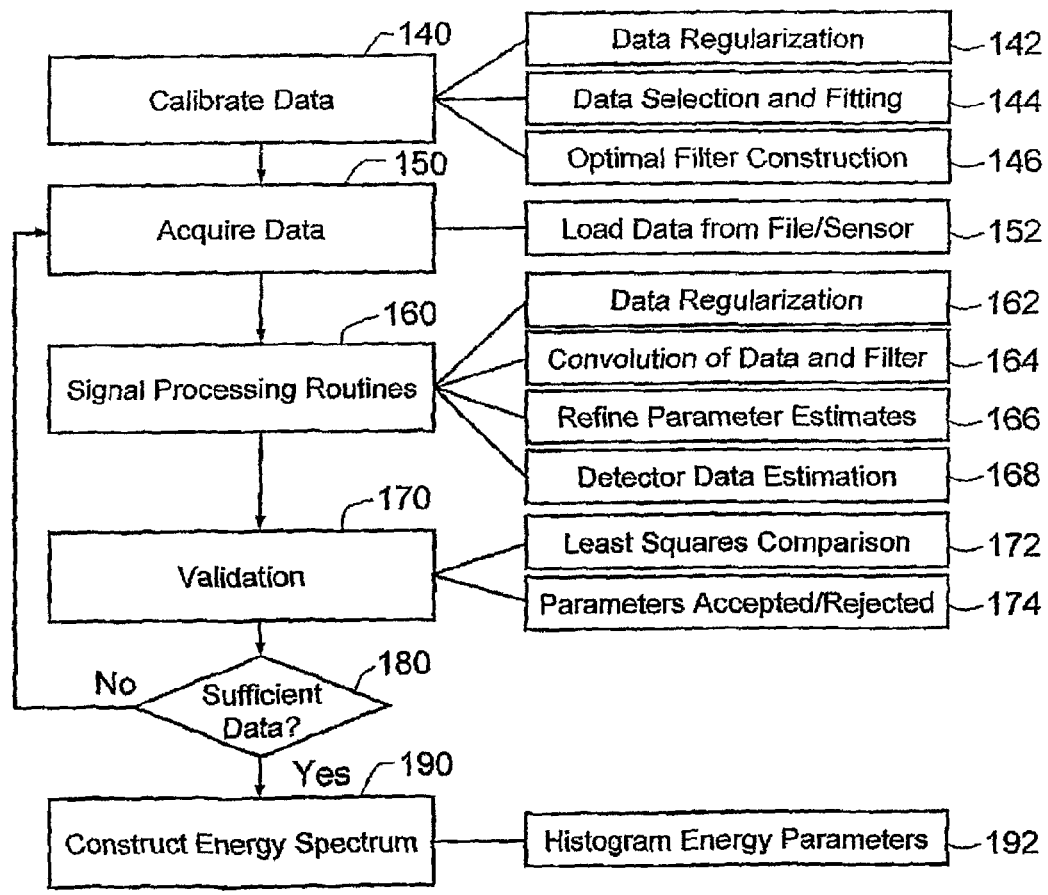
FIG. 9 is a schematic flowchart of the signal processing method for pulse pile-up recovery employed by the apparatus of FIG. 1 for analyzing spectroscopic data according to this embodiment of the invention.

FIG. 9 is a flow diagram of the signal processing method of this embodiment. At step 140, calibration is performed. This involves Data Regularization or Conditioning 142, Data Selection and Fitting 144 and Optimal Filter Construction 146. In Data Regularization 142, calibration data signals recorded at a low incident radiation flux are loaded from data files, the integrity of these calibration data is checked and any bias in the baseline of the data removed. Data Selection and Fitting 144 involves selecting only that data corresponding to the detection of single radiation events and constructing a data based model of the detector impulse response. A functional form of this model is then obtained by fitting a suitable function to the data, such as a polynomial, exponential or spline function. This results in the expected impulse response of the detector d[n]. Optimal Filter Construction 146 employs this detector impulse response to construct a suitable filter for the detector, such as an inverse fitter or a matched filter.

At step 150 data is acquired, but may be affected by significant pulse pile-up. The data may be input 152 either from a file or directly from the detector elements 16.

At step 160 signal processing routines are applied to determine the amplitude and timing parameters of the signals in the time series. Firstly the data is conditioned 162 to remove any bias in the baseline of the data. Next, the detector data is convoluted 164 with the filter derived in step 146 to provide an initial estimate of the time-of-arrival parameters ($\tau$) and number of pulses (N). The timing parameters and estimate of the number of pulses are then further refined 166 using a suitable peak detection process, and the energy parameter ($\alpha$) is determined from $\tau$, N and the detector impulse response d[n] (such as by linear programming, matrix inversion or convolution techniques). Finally, from the number (N), energy ($\alpha$), timing ($\Delta_i$) and detector impulse response (d[n]), an estimate of the detector data stream ($\hat{x}[n]$) is made 168.

The parameter vector ($\alpha$) may be determined by linear programming or by solving the system of linear equations defined in Equation 4 using a suitable method for solving such systems of equations, such as one of those described, for example, by G. H. Golub and C. F. Van Loan [*Matrix Computations*, 2nd Ed, Johns Hopkins University Press, 1989].

At step (170) the validation phase 128 referred to above is performed, which may be referred to as error checking as, in this embodiment, validation involves determining an error signal e[n], computed successively for the set of samples corresponding to each signal i where 1<i<N (N being the total number of signals in the data stream). This error signal is calculated by determining 172 the squares of the differences between the time series data x[n] and the model based datastream ($\hat{x}[n]$ from step 168); e[n] is thus the square of the difference between x[n] and $\hat{x}[n]$, as given in Equation 6.

$$e[n] = (x[n] - \hat{x}[n])^2 \quad (6)$$

If e[n] exceeds a predetermined threshold, these parameters are rejected 174 as this condition indicates that the signal parameters do not produce a model of the respective signal that acceptably conforms to that signal (that is, is sufficiently accurate); the relevant signal is deemed to constitute corrupted data and excluded from further spectroscopic analysis. The threshold may be varied according to the data and how closely it is desired that the data be modeled; generally, therefore, in any particular specific application, the method of validation and definition of the threshold are chosen to reflect the requirements of that application.

One example of such a threshold is the signal energy $\alpha_i$ multiplied by a suitable factor, such as 0.05. Validation will, in this example, deem that the model acceptably conforms to the data constituting signal i when:

$$e[n] < 0.05\alpha_i \quad (7)$$

Validation may be performed by defining the error signal and threshold in any other suitable way. For example, the error signal may be set to the absolute value of the error. The threshold may be defined to be a multiple other than 0.05 of the signal amplitude. Another threshold comprises a number of noise standard deviations.

Decreasing the threshold (such as by decreasing the coefficient of $\alpha_i$ in Equation 7) enables improved energy resolution at lower throughput, while increasing the threshold enables improved throughput at reduced energy resolution.

At step 180 a decision is made as to whether there is sufficient data. If not, processing continues at step 150. Otherwise, the method proceeds to step 190. At step 190 a gamma-ray energy spectrum is created. The gamma-ray energy parameters determined at step 166, which were deemed to be of sufficient accuracy at step 174, are represented 192 in the form of a histogram. This is the gamma-ray energy spectrum on which spectroscopic analysis may be performed.

Results of Signal Processing Method

Figure 10A:
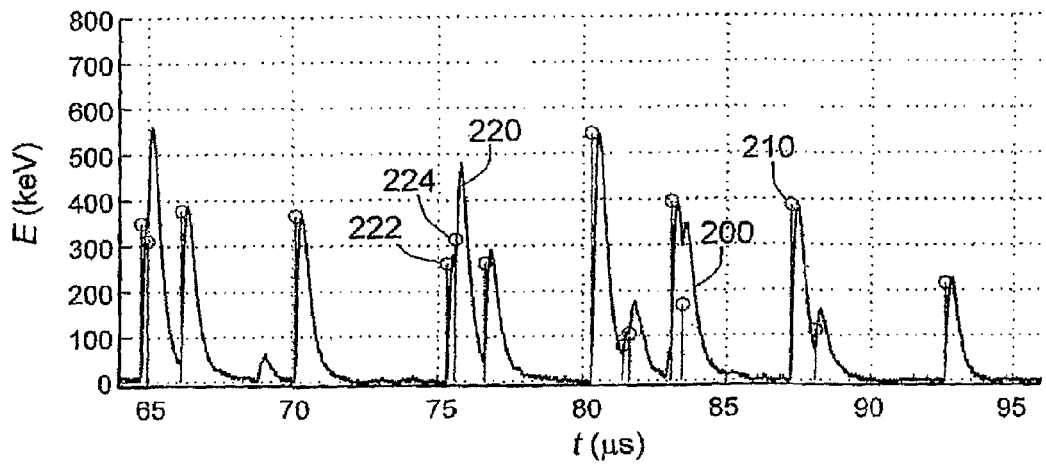
FIGS. 10a, 10b and 10c are plots of the results at different stages of the signal processing method of FIG. 9.
Figure 10B:
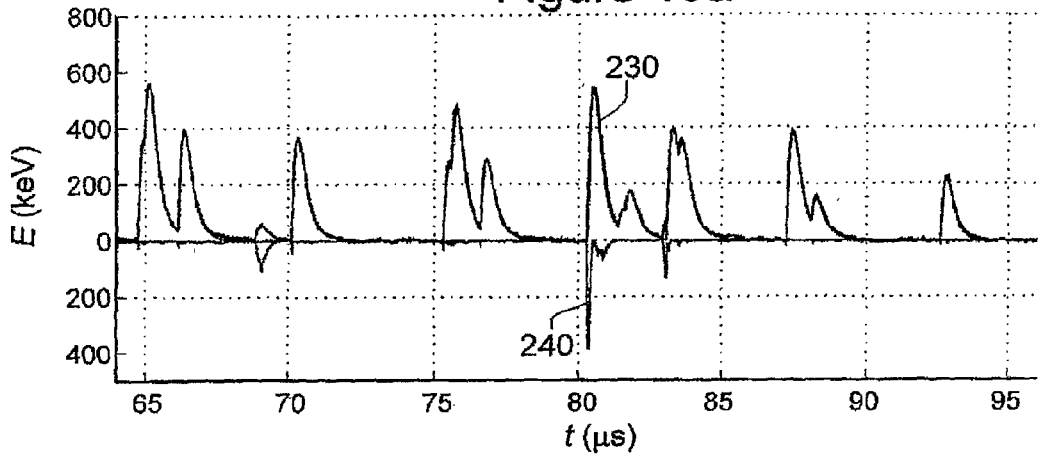
Figure 10C:
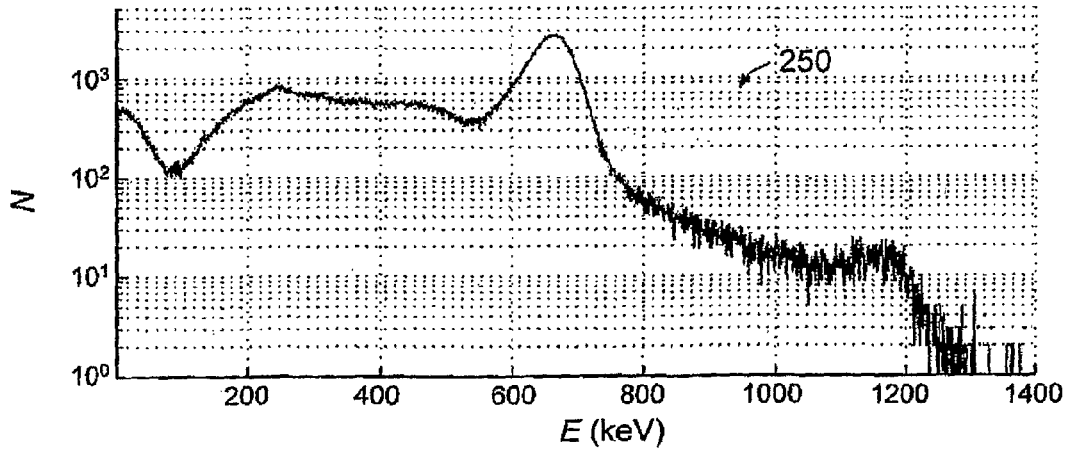

FIGS. 10*a*, 10*b* and 10*c* are plots of the results at various stages of processing of the digital signal processing method described above by reference to FIGS. 8 and 9, for digitized data collected with a scintillation gamma-ray detector. The detector data stream was digitized by an analog to digital converter at 125 MHz and 0.12 bit accuracy; the gamma-ray source used was a 137Cs source with a primary gamma-ray emission of 661.7 keV.

Scintillation detectors employ light generated by the detector/radiation interaction to detect and measure that incident radiation. A scintillation detector may comprise organic scintillators or inorganic scintillators. Organic scintillators include both organic crystalline scintillators and liquid organic solutions (where the scintillating material has been dissolved to form a liquid scintillator, which can then be plasticized to form a plastic scintillator. Inorganic scintillators include crystalline scintillators such as NaI(TI), BGO, CsI(TI) and many others, and photo switch detectors (in which a combination of two or more dissimilar scintillators are optically coupled to a common PMT to exploit the differing decay times of the scintillators to determine where a radiation/detection interaction has occurred).

In this example the detector comprised a 76 mm×76 mm NaI(TI) gamma-ray scintillation detector. FIG. 10*a* is a plot of a portion of the digitized detector data 200 prior to processing by the signal processing method plotted as energy E(keV) versus time t($\mu$s), together with the results (for example, at 210) of the signal processing method plotted in terms of the temporal position and energy of the component signals. For example, what may appear to be a single peak 220 in the original digitized detector data 200 at approximately 75.8 µs has been resolved into two distinct signals 222, 224 at respectively 75.3 and 75.7 µs.

From the determined temporal positions, energies and forms of the signals it is possible to generate a model of the detector data. FIG. 10*b* is a plot of the resulting data model 230, shown as energy E(keV) versus time t(µs), of that portion of the digitized detector data stream 200 shown in FIG. 10*a*. An inverted error plot 240, comprising a plot of the squares of the differences between the detector data 200 and the data model 230, is also shown, and indicates the error in the model 230. The error signal is small where the model 230 has tracked the output of the detector accurately, but the error becomes large when there are inconsistencies between the model 230 of the detector data and the detector data 200 itself. Based on this error signal 240, a decision can be made as to whether to accept or reject the signal parameters estimated by the signal processing method.

FIG. 10*c* is a gamma-ray energy spectrum 250 shown as a log-linear plot, produced by the signal processing method. The energy parameters that have been accepted are plotted as a histogram, where the horizontal axis represents the energy E(keV) of each signal in a respective bin, and the vertical axis represents the number of counts N of that energy determined to have been detected in the collection period (in this example, 1 s).

Figure 11:
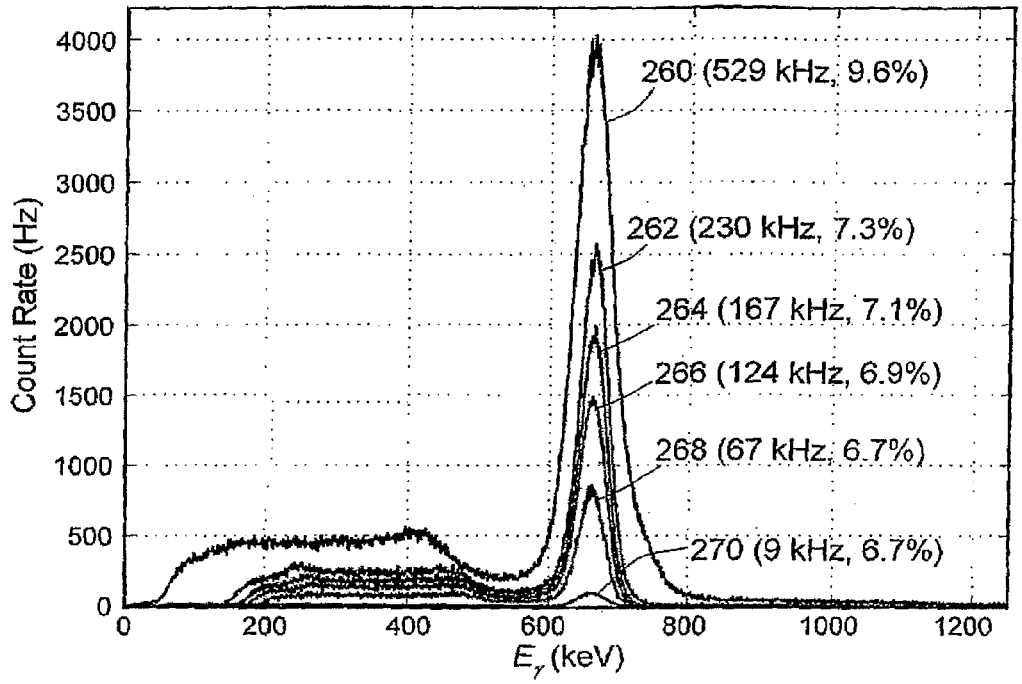
FIG. 11 are plots of gamma-ray spectra for a 137Cs source at various input count rates, processed with the method of FIG. 9.

FIG. 11 is a plot of exemplary gamma-ray energy spectra, collected using a sodium iodide NaI(TI) gamma-ray detector. The gamma-ray energy spectra shown in FIG. 11 demonstrate the performance of the signal processing method for pulse pile-up recovery at a range of count rates. The experimental data were collected using a 76 mm×76 mm Canberra brand NaI(TI) gamma-ray detector (model number 802) coupled to a detector base (model number 2007); no preamplifier was used. The signal processing hardware was connected to the dynode output of the detector base via a 65 MHz 14-bit analog to digital converter.

The NaI(TI) crystal was irradiated with a collimated gamma-ray beam, which ensured that the central portion of the detector was illuminated with an essentially parallel beam of gamma-rays; the beam diameter was 50 mm.

Two 137Cs gamma-ray sources of 0.37 GBq and 3.7 GBq, in combination with three calibrated aluminium transmission filters, were used to obtain a range of gamma-ray fluxes at the detector face. The detector to source distance remained constant during data collection.

Referring to FIG. 11 the spectra 260, 262, 264, 266, 268 and 270 were collected at count rates of respectively 529 kHz, 230 kHz, 167 kHz, 124 kHz, 67 kHz and 9 kHz. As would be expected, the energy resolution of the data collected with the apparatus and processed with the method of this embodiment deteriorated as the count rate increased. Expressed as a percentage of the peak energy (i.e. 661.7 key), the full width at half maximum (FWHM) of the peak was found to be, respectively, 9.6% 7.3%, 7.1%, 6.9%, 6.7% and 6.7%. For count rates of 9 kHz to 230 kHz, the energy resolution of the 137Cs gamma-ray energy peak at 661.7 keV remained less than 7.5%; that is, despite more than a 25 fold increase in the count rate from the NaI(TI) detector, the energy resolution at 661.7 keV is degraded by less than 0.5%.

Figure 12:
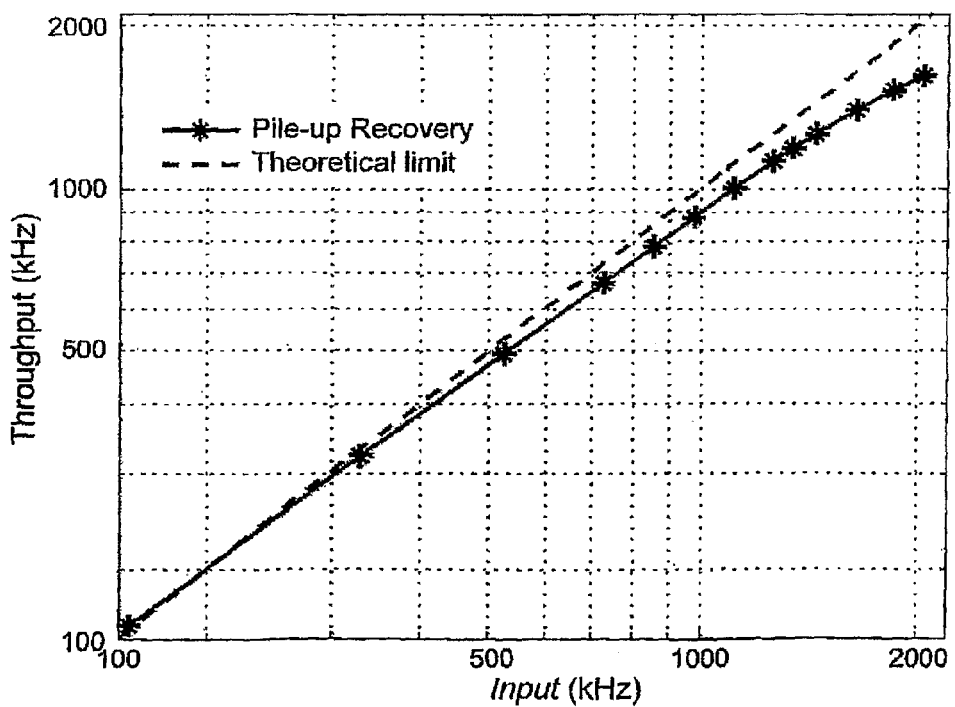
FIG. 12 is a plot of the results of a computer simulation of the signal processing method of FIG. 9 prepared using a simulated data set produced by a digital nuclear pulse generator.
Figure 13:
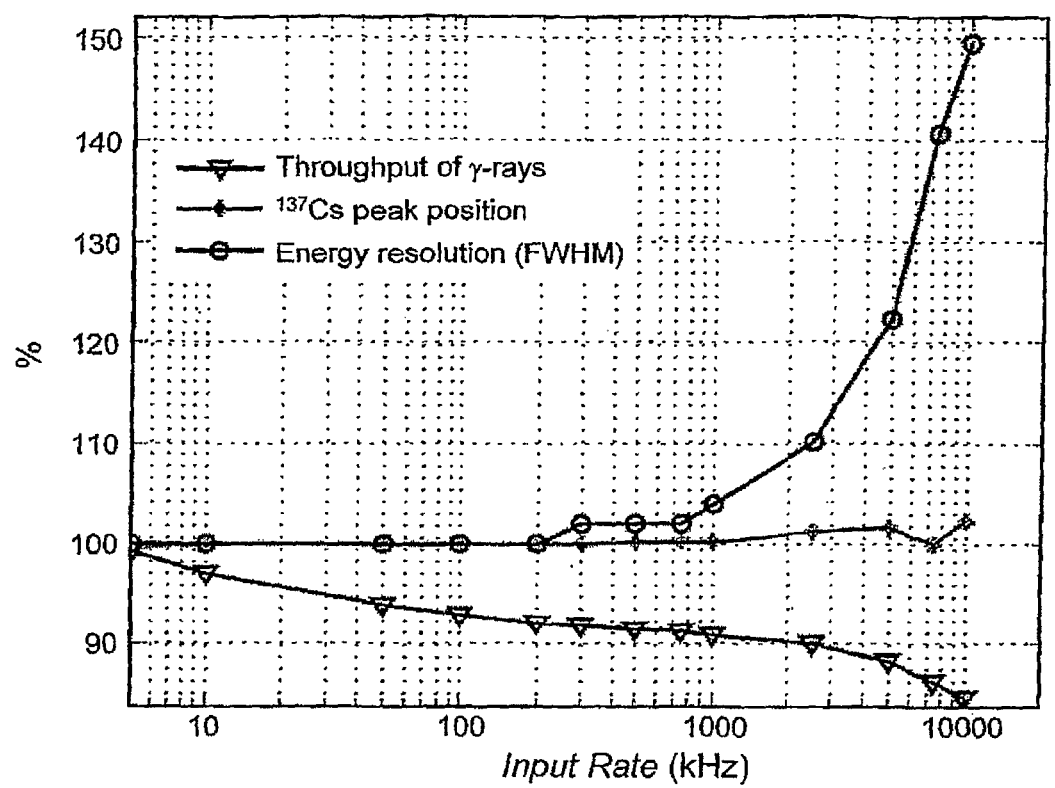
FIG. 13 is plot of the performance of the simulation of FIG. 12 for a gamma-ray source over a range of count rates.

The performance of the signal processing method of this embodiment is also illustrated in FIG. 12 and FIG. 13. These two figures were generated from the results of a computer simulation, in which the input count rate could be accurately controlled hence enabling a very wide range of input count rates to be considered. FIG. 12 is a log-log plot of the throughput of the signal processing method (i.e. that portion of the input count rate accurately detected) against input count rate from 0.1 to 2.5 MHz. The ideal limit (i.e. where the throughput equals the input) is shown with a dashed line. This figure demonstrates that, over a very wide range of input count rates, the throughput of the signal processing method remains greater than or equal to 90%.

FIG. 13 is a linear-log plot comparable to FIG. 12 but with percentage throughput plotted against input count rate from 0.005 to 10 MHz. In addition, FIG. 13 includes plots of the energy resolution and peak position performance of the signal processing method of this embodiment. The energy resolution of the 137Cs peak degrades by less than 10% over 0 to 2.5 MHZ, and the peak position shows very little change over that range.

FIGS. 14*a*, 14*b*, 14*c* and 14*d* also depict the results of applying the signal processing method for pulse pile-up recovery of this embodiment to the output of a 76 mm×76 mm NaI(TI) gamma-ray detector. Approximately 14 µs of data was used to generate the data plotted in these figures. The figures are plots of energy E in arbitrary units against time t(µs).

Figure 14A:
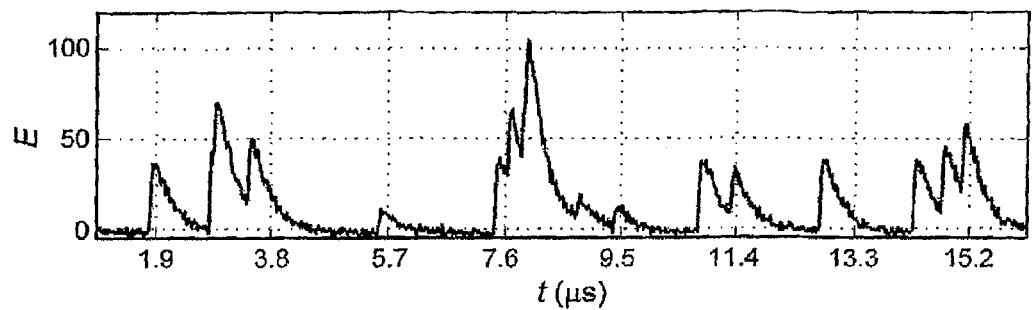
FIGS. 14a, 14b, 14c and 14d depict the results of applying the signal processing method of FIG. 9 to the output of a 76 mm×76 mm NaI(Tl) gamma-ray detector.
Figure 14B:
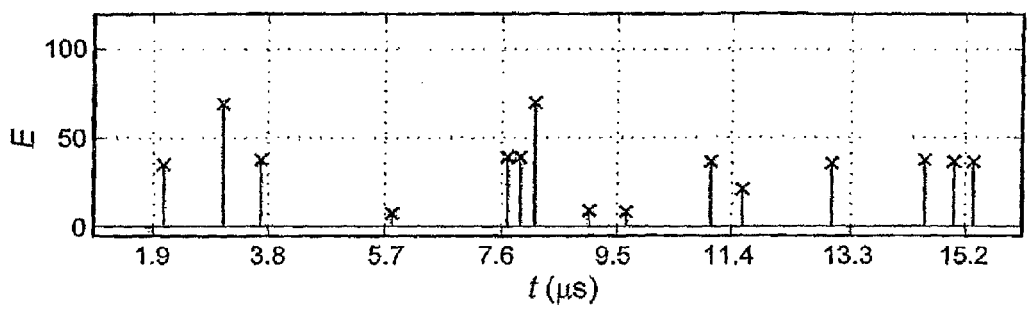
Figure 14C:
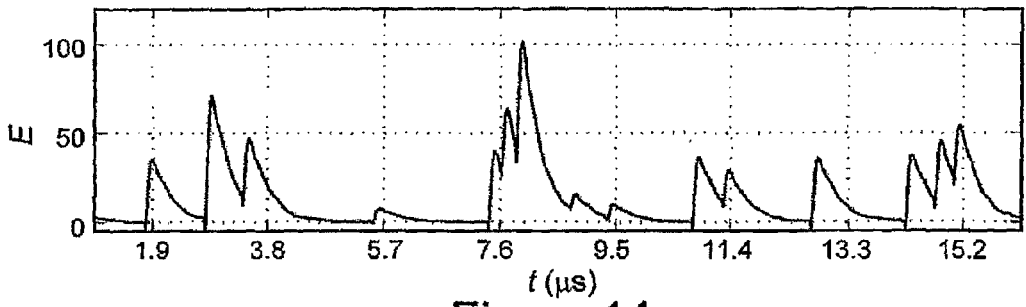
Figure 14D:
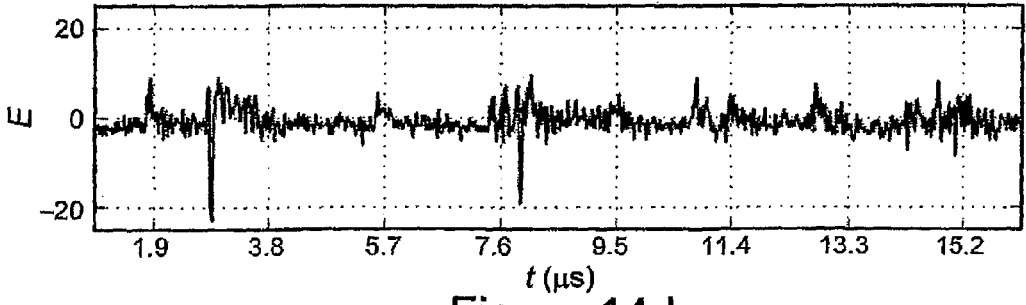

FIG. 14*a* is a plot of the output of AFE 94: an analog to digital conversion rate of 65 MHz and 14 bit resolution was used to convert the time varying voltage output of the detector to digital data. FIG. 14*b* is a plot of the results of applying the method. The temporal positions of the signals (depicted as vertical lines) have been resolved, as have the energies of the component signal (depicted as crosses). The temporal position and the energy of the component signal were used as described above, in conjunction with the signal form, to determine a model of the gamma-ray detector output: the resulting model is plotted in FIG. 14*c*.

The digitized output of the gamma-ray detector was compared with the model of the gamma-ray detector output to derive an estimate of the error made in characterizing the gamma-ray detector output. This error signal is plotted in FIG. 14*d*. It is then possible, on the basis of this error signal, to determine thresholds for the exclusion of signal parameter estimates, such as the decision to accept or reject an estimate of signal energy may be determined by the magnitude or the error near the position of a signal peak.

FIGS. 15*a*, 15*b*, 15*c* and 15*d* depict the results of applying the signal processing method for pulse pile-up recovery of this embodiment to data collected with a semiconductor (or solid state) detector. Such detectors employ the interaction of incident radiation with the electrons in the crystalline lattice of the semiconductor, forming electron hole pairs. Examples of these detectors include High-Purity Germanium (HPGe) detectors, Silicon Diode detectors, semiconductor drift detectors (such as Silicon Drift detectors), Cadmium Telluride (CdTe) detectors and CZT detectors.

Figure 15A:
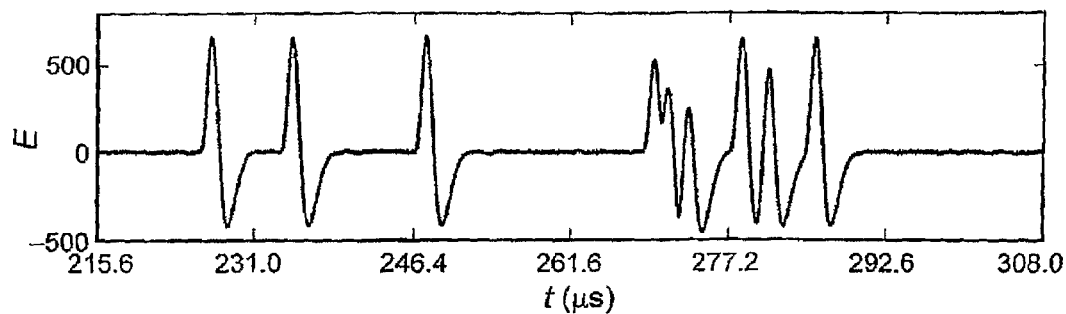
FIGS. 15a, 15b, 15c and 15d depict the results of applying the signal processing method of FIG. 9 to data collected with a HPGe detector.
Figure 15B:
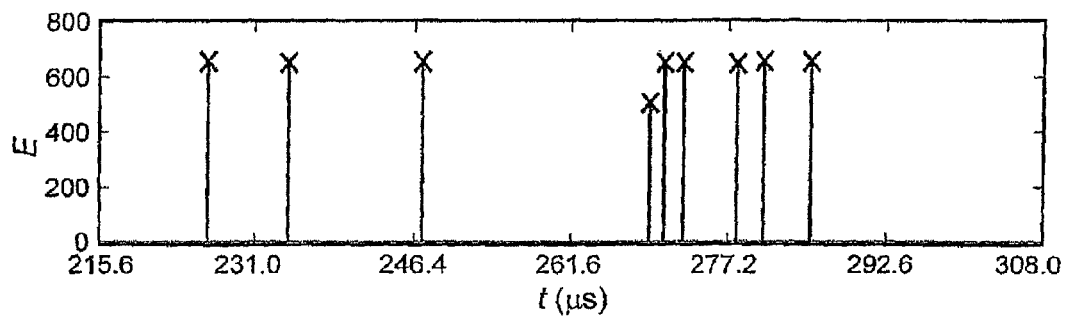
Figure 15C:
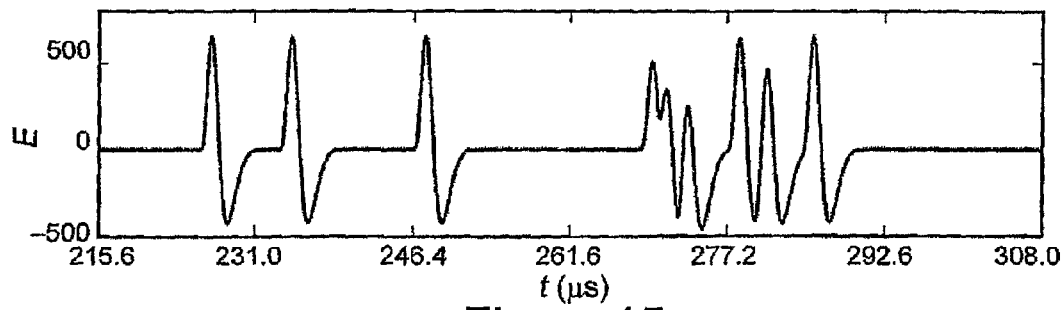

Hence, the apparatus of FIG. 1 was employed, though with a detector unit in the form of a Canberra industries brand High Purity Germanium (HPGe) detector substituted for detector module 16, and with a 57Co gamma-ray source (whose two principal gamma-rays have energies of 122.1 and 136.5 keV) rather, than a subject 12. The output of the HPGe detector was fed through a pre-amplifier and then into an Ortec brand pulse shaping amplifier. Approximately 92 µs of data was collected, from which was generated the data plotted in FIGS. 15*a*, 15*b*, 15*c* and 15*d* as energy E in arbitrary units against time t(µs). FIG. 15*a* is a plot of the output of AFE 94. The time varying voltage output of the detector was converted to digital data at an analog to digital conversion rate of 65 MHz with 14 bit resolution. FIG. 15*b* is a plot of the results of applying the method. The temporal positions of the signals (depicted as vertical lines) have been resolved, as have the energies of the component signal (depicted as crosses). The temporal position, the energy of the component signal and the signal form were used to determine a model of the processed HPGe detector output, which is plotted in FIG. 15c.

Figure 15D:
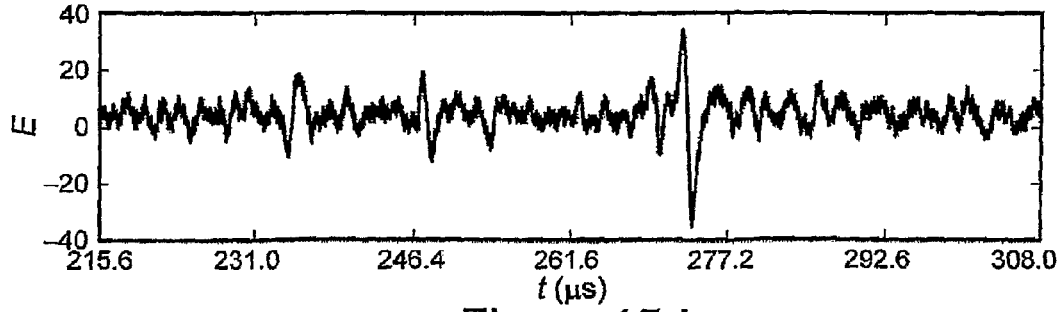

FIG. 15d is a plot of the error signal, derived from a comparison of the digitized processed output of the HPGe detector and the model of that output. This error signal can again be used to determine thresholds for the exclusion of signal parameter estimates.

FIGS. 16a, 16b, 16c and 16d depict the results of applying the signal processing method for pulse pile-up recovery of this embodiment to the output of a gas proportional detector used for detecting X-rays. Gas proportional detectors are a class of detector whose behavior is similar to that of solid state detectors. Gas proportional detectors rely on the interaction of the radiation with a gas in a chamber. An electric field is created in the chamber between an axial wire and the walls of the chamber. Radiation passing through the gas ionizes the gas, which produces electrons that then collect on the wire owing to the electric field, and are output as the detector data.

Thus, a simplified form of apparatus 10 of FIG. 1 was employed, with a detector in the form of a Xenon gas proportional detector substituted for detector modules 16, and with an X-ray generator from an X-ray diffraction apparatus rather than a subject 12. Approximately 300 µs of data was used to generate the data plotted in FIGS. 16a, 16b, 16c and 16d, which plot energy E in arbitrary units against time t(µs). A significantly longer data collection period was used compared with that of the previous examples, owing to the relatively long decay time of the xenon gas proportional detector (of the order of 50 µs or more). For this reason also the sampling rate of AFE 94 was reduced.

Figure 16A:
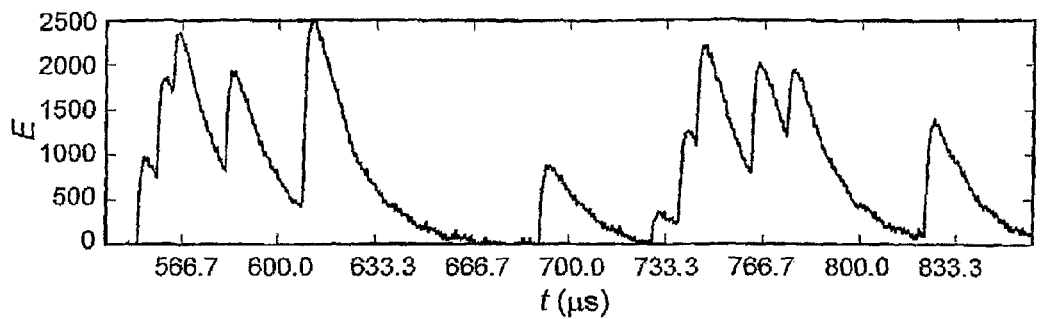
FIGS. 16a, 16b, 16c and 16d depict the results of applying the signal processing method of FIG. 9 to the output of a Xenon gas proportional detector.
Figure 16B:
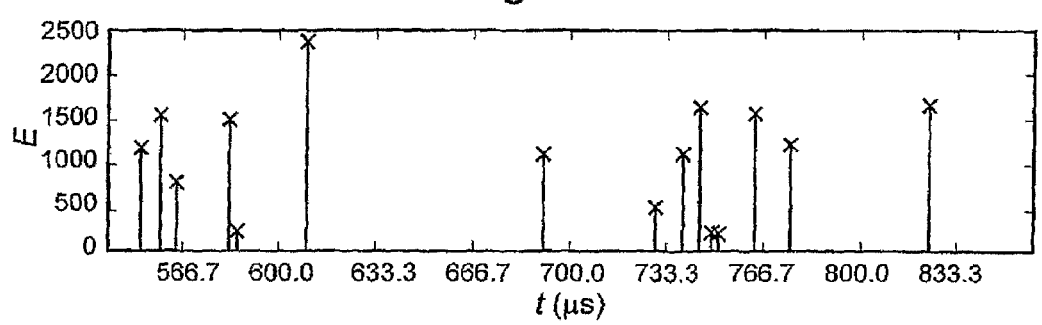
Figure 16C:
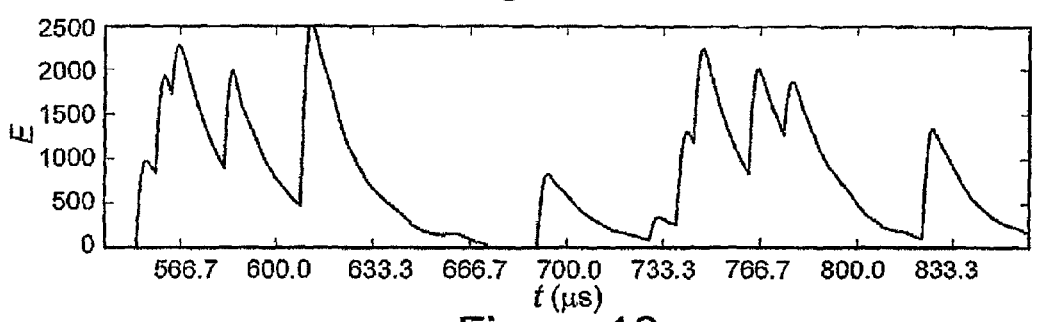
Figure 16D:
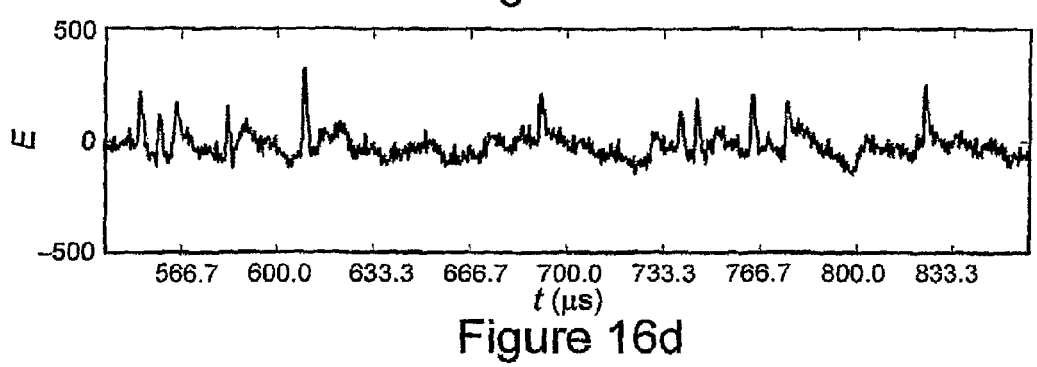

FIG. 16a is a plot of the output of AFE 94; in this example an analog to digital conversion rate of 15 MHz and 14 bit resolution was used to convert the time varying voltage output of the detector to digital data. FIG. 16b is a plot of the results of applying the method. The temporal positions of the X-ray signals (depicted as vertical lines) have been resolved, as have the energies of the component signal (depicted as crosses). The temporal position and the energy of the component signal were used as described above, in conjunction with the signal form, to determine a model of the Xenon gas proportional detector output: the resulting model is plotted in FIG. 16c.

The digitized output of the Xenon gas proportional detector was compared with the model of the Xenon gas proportional detector output to derive an estimate of the error made in characterizing the Xenon gas proportional detector output. This error signal is plotted in FIG. 16d. This error signal can then be used to determine thresholds for the exclusion of signal parameter estimates, such as the decision to accept or reject an estimate of signal energy may be determined by the magnitude or the error near the position of a signal peak.

Plural Signal Forms

For some detector types, such as large volume solid state detectors, the form of a given signal may be one of a plurality of possible signal forms. This may be intrinsic to the detector type, or be due to temperature or other measurement-specific factors.

For example, a CsI(Tl) detector is a scintillation detector that, depending on whether a neutron or gamma-ray is being detected, exhibits two distinct signal forms. Solid state radiation detectors can exhibit a time-varying signal form, even when detecting only one form of radiation; large volume High Purity Germanium (HPGe) detectors, for example, can produce an output signal whose form depends on the specific site of interaction between the radiation and the detector. The interaction of radiation with the Germanium crystal of a HPGe detector produces a multitude of electron-hole pairs; radiation induced charge is carried by both the electrons and the holes. However, the electrons and holes travel through the HPGe detector at different velocities, so the charge pulse produced by the electrons generally has a different form from that produced by the holes. Thus, the pulse produced by the detector (being the sum of the charges carried by both the electrons and holes) has a form dependent on the location of interaction.

Hence, the plurality of signal forms are the result of these varied physical mechanisms. The respective signal forms may be denoted $d_1[n], d_2[n], \ldots, d_Q[n]$, where Q is the total number of different signal forms that may be generated by a particular detector type. Each of the possible signal forms is characterized in the same way that the signal form of data having a single signal form is characterized. With plural signal forms, however, the calibration process must be extended for an appropriate length of time to ensure that all of the possible signal forms have been identified and characterized; the estimation of signal parameters, including temporal position and signal energy, can be performed once the form of each signal in the data stream has been identified. In order to estimate these signal parameters correctly, a number of possible extensions of the method described above (for data with a single signal form) may be employed.

1. The signal parameters, including signal temporal position and signal energy, may be estimated for each signal in the data stream by treating all signals in the data stream as having the same form, such as of the first signal, viz. $d_1[n]$. The parameters for those signals that do not acceptably conform to signal form $d_1[n]$ are rejected at the validation phase; signals for which the parameters have been estimated successfully and thus acceptably conform to signal form $d_1[n]$ are subtracted from the data stream. This process is repeated successively for $d_2[n]$ up to $d_Q[n]$, where at each stage signal parameters are estimated for signals that are of the signal form used at that stage. At each stage matrix Equation 4 is solved with matrix A constructed repeatedly using, in iteration p, the signal form $d_p[n]$. At the conclusion of the process, those signals that have not passed the validation phase for any of the pluralityy of signal forms are rejected as not acceptably conforming to any of the plurality of signal forms.

2. In a variation of the first approach, the signal parameters are estimated for each of the signal forms in turn, but the signal estimates are not subtracted at each stage. Instead, the estimated signals are used in a final signal validation stage to determine the signal form and signal parameters that provide the best overall estimate of the data stream. This allows for the possibility that a signal is incorrectly estimated to be of one form, when it is actually of a form that has not yet been used to estimate the signal parameters.

3. In a further variation of the first approach, it may be possible to model each of the signal forms $d_p[n]$ as a linear combination of two signal forms, termed $d_1[n]$ and $d_2[n]$ for convenience. Hence, the pth signal form $d_p[n]$ is modeled as:

$$d_p[n]=(a.d_1[n]+b.d_2[n]) \qquad (8)$$

where a and b are unknown constants that can be determined directly from this equation if necessary. In order to solve the matrix equation in this case, the matrix equation is extended to be:

$$x = [\, A_1 \;\vdots\; A_2 \,] \begin{bmatrix} \gamma \\ \ldots \\ \beta \end{bmatrix} + \omega, \quad (9)$$

where the sub-matrices $A_1$ and $A_2$ are formed from the signal forms $d_1[n]$ and $d_2[n]$ respectively using Equation 5. The vector of unknown signal energies $\alpha$ has been redefined as being made up of vectors $\gamma$ and $\beta$, so that the energy of the actual signal form of signal i can be estimated as $\alpha_i = \gamma_i + \beta_i$. The new system of linear equations is solved using the same methods as those used to solve the earlier matrix equation, Equation 4. It should be noted that this approach allows for the possibility that the signal form may be from a continuum of possible signal forms that can be represented as a linear combination of the two signal forms $d_1[n]$ and $d_2[n]$.

Thus, this approach permits a practically unlimited number of signal forms to be represented.

4. In a further variation of approach 3, the procedure of decomposition of each of the plurality of signal forms into a linear combination of just two signal forms may be extended to the general case where the plurality of signal forms may be decomposed as a linear combination of an arbitrary number of signal forms. The matrix A and the signal energy vector a is augmented accordingly.

EXAMPLE

In single photon emission computer tomography (SPECT), a radio-active tracer, such as technetium 99m (Tc99m) having a 140.5 keV gamma-ray emission and a 6.01 h half-life, is injected into a patient; after a suitable delay to enable the tracer to spread, the distribution of the tracer within the patient's body is imaged with a gamma-ray camera.

The gamma camera is rotated around the patient, and multiple 2D views (projections) of the patient are taken from different angles. A computer is then used to construct these individual 2D projections into a 3D image. The specific camera and radio-isotope settings will vary according to camera and application. However, a typical acquisition protocol for a bone scan may specify 1200 MBq of (Tc99m) tracer, 120 different 2D projections as the camera is rotated 360° around the patient, and a collection time per projection of 20 s. The total time required for this scan is thus 40 min or, with at gamma-ray camera that has two heads, about 20 min. As will be readily appreciated, it is very important that there be no patient movement during the scan, as such movement will cause significant degradation of the ultimate 3D image.

Figure 17:
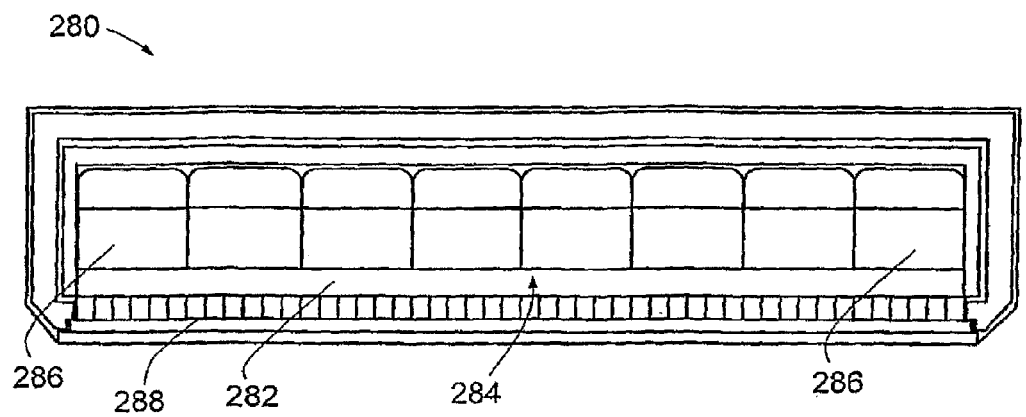
FIG. 17 is a schematic, cross-section view of a gamma-ray camera of the background art for use in SPECT.
Figure 18:
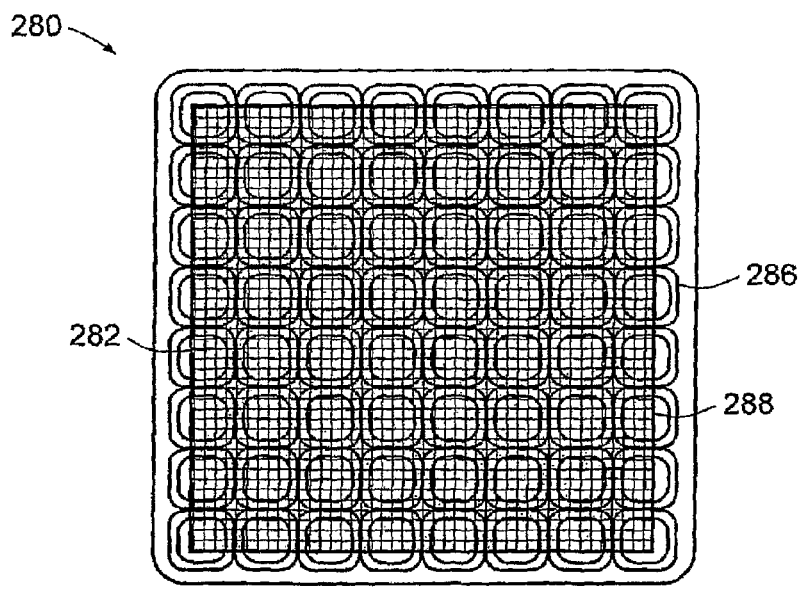
FIG. 18 is a schematic, face-on view of the gamma-ray camera of FIG. 17.

FIG. 17 is a schematic, cross-section view of such a gamma-ray camera 280 of the background art. FIG. 18 is a schematic, face-on view of camera 280. Camera 280 comprises a single, large crystal 282 of scintillation material (in this example, Sodium Iodine (NaI)) and an 8×8 array 284 of photomultiplier tubes 286. Photomultiplier tubes 286 are situated optically behind crystal 282 to detect scintillation emitted by scintillation crystal 282 due to the interaction of gamma rays with scintillation crystal 282; photomultiplier tubes 286 convert the scintillation light into electrical signals.

Scintillator crystal 282 is of the order of 10 mm thick to insure that a significant proportion of the incoming gamma-rays of interest (in this example, 140.5 keV gamma rays) are absorbed and detected by camera 280. Spatial information about the distribution of the tracer within the patient is obtained by correlating detected photons with their points of origin; this is facilitated by providing camera 280 with a lead collimator 288. Thus, photomultipler tubes 286 output an energy signal and an x,y-coordinate pair.

Figure 19A:
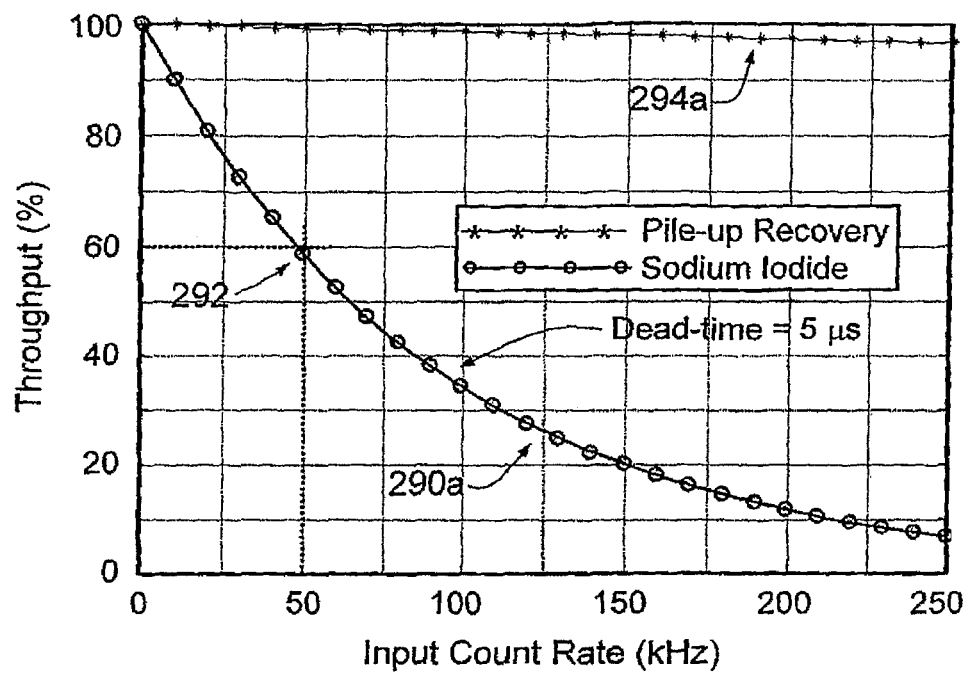
FIGS. 19a and 19b are plots of percentage throughput as a function of input count rate calculated for the gamma-ray camera of FIG. 17 assuming a dead-time of 5 µs, and of the calculated performance of the signal processing method for pulse pile-up recovery of an embodiment of the present invention.
Figure 19B:
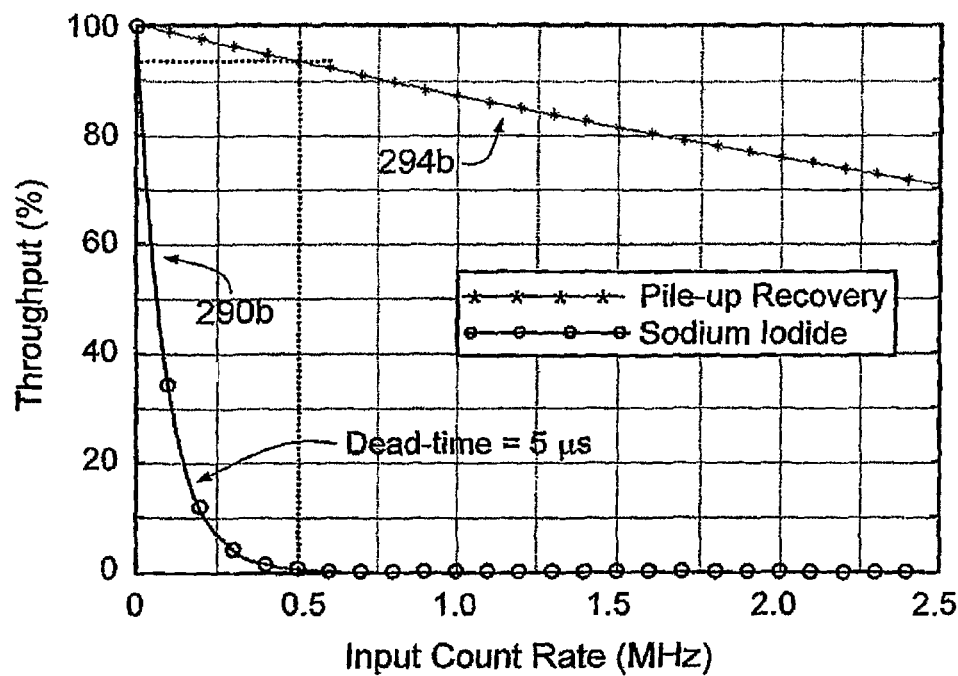

A significant source of dead-time in SPECT systems is the processing of the detected events in the front-end electronics; typical dead-times for systems based on NaI crystals are of the order of 4 to 8 µs, which is dictated by the amount of integration time required to collect the light from a scintillation event. Hence, the shorter the integration time the lower the dead time. Based on these characteristics (and assuming a dead-time of 5 µs), the percentage of incoming radiation events that are not impeded by pulse pile-up, that is, the throughput of camera 280, was modelled: the resulting plots are shown in FIGS. 19a and 19b (plotted as circles), at 290a and 290b respectively. From FIGS. 19a and 19b it is apparent that approximately 40% of all the events impinging on camera 280 will be lost owing to pulse pile-up at an input count-rate of 50 kHz (as shown at 292).

Figure 20:
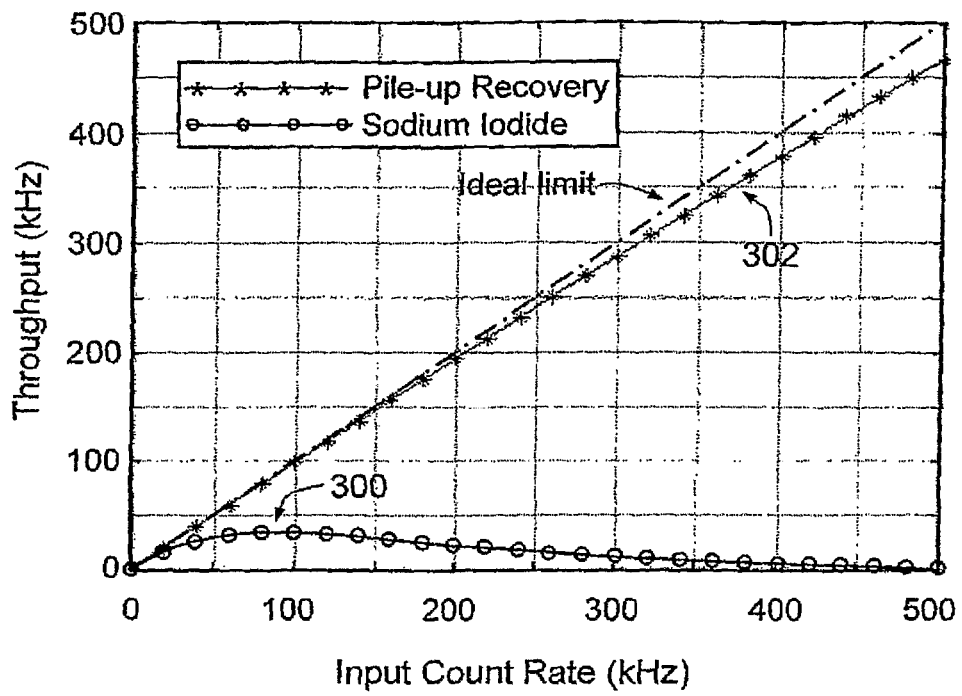
FIG. 20 are plots of throughput count rate as a function of input count rate, calculated for the gamma-ray camera of FIG. 17 assuming a dead-time of 5 µs, and of the calculated performance of the signal processing method for pulse pile-up recovery of an embodiment of the present invention.

FIG. 20 depicts throughput count rate (kHz) versus input count rate (kHz), calculated using the same detector parameters; an input count rate is soon reached (at about 90 kHz) at which any further increase in the incoming event rate does not increase the number of detected events (see point 300). The NaI camera 280 has a dead-time assumed to be a fixed 5 µs, so as the input count rate increases the probability of pile-up gets ever greater; this is because, as the input count rate increases, the data corrupted by pulse pile-up must be discarded and cannot be used in the SPECT camera.

The performance of the signal processing method for pulse pile-up recovery of the embodiment of FIG. 9 has been calculated and is plotted as stars in FIGS. 19a and 19b, at 294a and 294b respectively. At the same input count rate where the NaI detector alone (with conventional electronics) has a dead-time of 40% (viz. ~50 kHz), pulse pile-up recovery of this embodiment has a throughput of greater than 98%.

This is (98-60)/60=63.3% better than the performance of camera 280 alone, so—at this count-rate and for the same detection statistics—an individual collection time (i.e. "dwell time") per projection equal to 60/98=61.2% of the previous time is possible. This amounts to 61.2%×20 s=12.2 s for the bone scan described above. Conservatively, a 25% saving in collection time for each projection may thus be expected (or, say, 15 s per projection), and perhaps as high as 35% in certain applications (or, say, 13 s per projection). A corresponding reduction in total scan time may be expected (though with a somewhat lesser time saving owing to the time required to rotate the camera about the patient between collections).

Furthermore, it is envisaged that the method of this embodiment will allow the collection of such scans at significantly higher count-rates (whether by increasing tracer activity or reducing patient to camera distance) than was possible heretofore. Referring to FIG. 20, the efficacy of the method of this embodiment—plotted at stars at 302—is still about 93% at as high an input count rate of 500 kHz. Consequently it should be possible to double the count-rate from the previously discussed 50 kHz to 100 kHz, yet still achieve a throughput of greater than 95% (a modest drop from the throughput at 50 kHz). This should thus allow an approximate further halving of the collection time for each projection to 12.2×0.5 (98/95)=~6.3 s. Neglecting rotation time, this implies a total scan time in the above scenario of 6.3×120≈12.6 min with a single head SPECT camera or 6.3 min with a SPECT camera with two heads.

EXAMPLE

Figure 21:
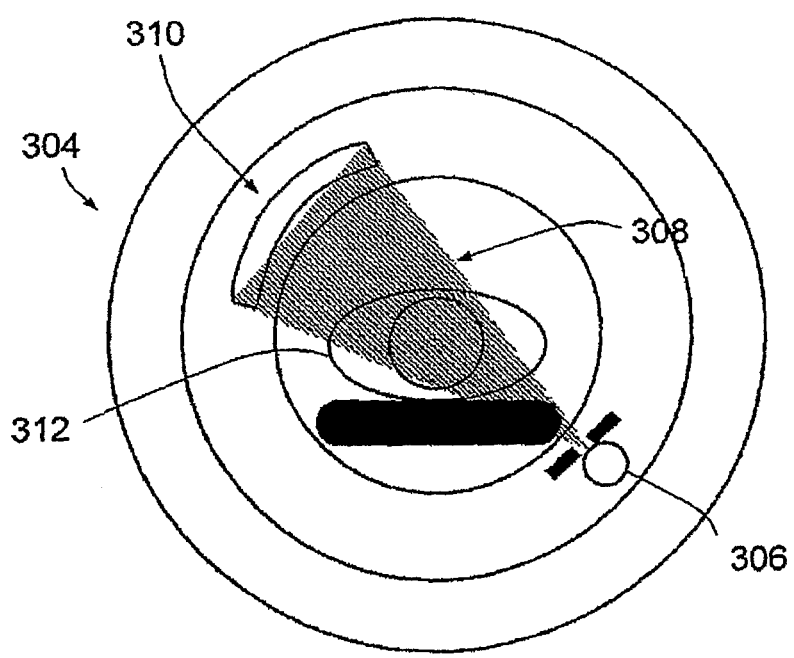
FIG. 21 is a schematic cross-sectional view of a Computed Tomography (CT) X-ray machine according to an embodiment of the present invention.

X-ray computed tomography is a medical imaging technique that uses a computer to stitch together multiple 2D images (projections) into a 3D image. FIG. 21 is a schematic view of a CT machine 304 according to an embodiment of the present invention. CT machine 304 includes an X-ray source in the form of an X-ray generator 306, to produce a fan beam of X-rays 308, and X-ray detectors 310 positioned on the opposite side of the machine from source 306 for detecting X-rays from X-ray generator 306 that have interacted with a subject 312 (shown as a recumbent patient). In use, projections are generated by using X-ray generator 306 to produce X-rays 308, and to detect X-rays with X-ray detectors 310. Both X-ray generator 306 and detectors 310 rotate around the subject, while maintaining their relative positions.

Figure 22A:
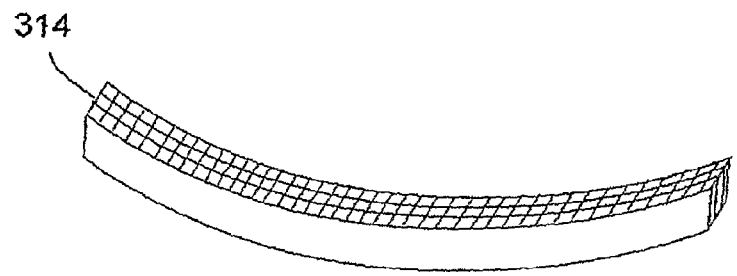
FIG. 22a is a schematic view of a detector used in the CT X-ray machine of FIG. 21.
Figure 22B:
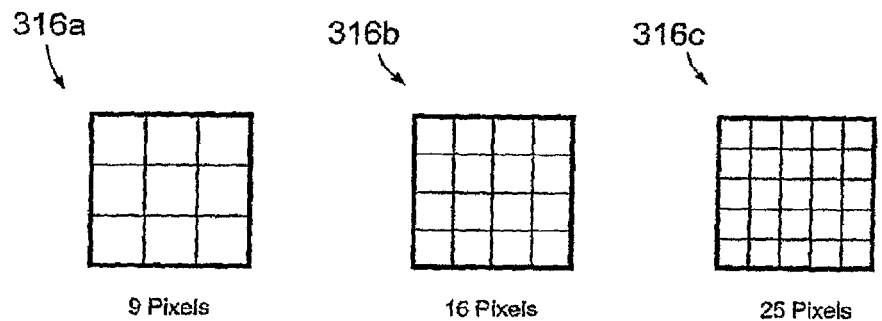
FIG. 22b is a schematic view of a detector element of the detector of FIG. 22a, depicting array sizes of 9, 16 and 25 pixels.

FIG. 22a is a schematic view of an exemplary detector 314 of detectors 310 of CT machine 304. There may be multiple detectors used in one CT machine in order to capture multiple slices (or projections) at the same time. FIG. 22b depicts the detector elements 316a, 316b, 316c of detector 314; detector elements 316a, 316b, 316c in this embodiment are between 1 mm and 10 mm square and comprise a plurality of pixels. Depending on application, CT machine 304 may have detector elements each comprising an array of 9 pixels 316a, 16 pixels 316b or 25 pixels 316c. The detector elements used in the CT X-ray machine may be made from a range of materials; they may be scintillation based X-ray detectors such as Caesium Iodine (CsI) or other like scintillators, constructed from a semiconductor radiation detector material such as Cadmium Zinc Telluride (CZT), High Purity Germanium (HPGe), Silicon Drift Detector (SDD) or of another semiconductor detector material.

Figure 23:
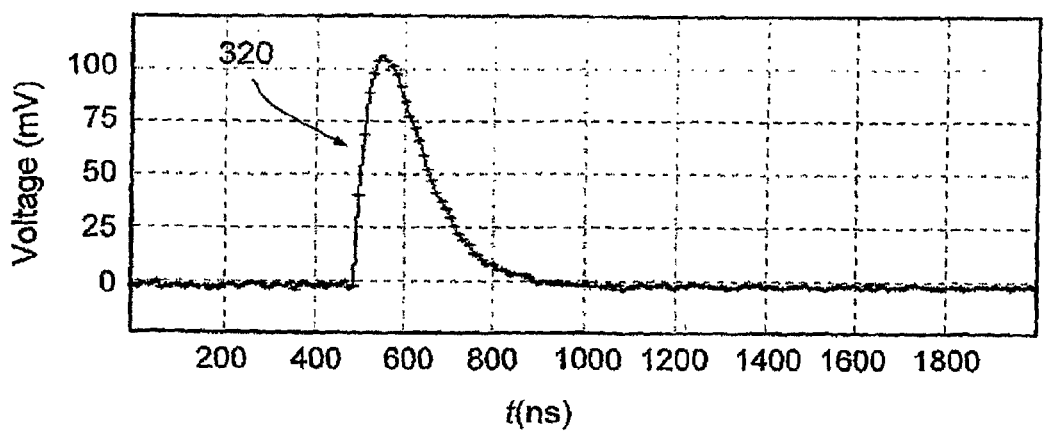
FIG. 23 is a plot of a model of the electrical signal produced by the detector used in a CT X-ray machine of FIG. 21.

FIG. 23 depicts a typical electrical output from a single pixel of a detector element 316a, 316b, 316c. The nuclear decay pulse 320 has a rise time of approximately 75 ns and a pulse duration of the order of 750 ns. The level of noise on the pulse is in the order of ±2% of peak amplitude and the energy is in the range from 10 keV to approximately 130 keV. The X-ray flux expected in modern X-ray CT machines can be as high as 100 million X-ray events per $mm^2$ of detector. If a detector element has 25 pixels (cf. element 316c of FIG. 22), the event rate through any given pixel will be of the order of 4 MHz; if the detector element has 16 pixels (cf. element 316b of FIG. 22), the event rate through any give pixel will be of the order of 6.25 MHz; if the detector element has 9 pixels (cf. element 316a of FIG. 22), the event rate through any given pixel will be of the order of 11 MHz.

Figure 24:
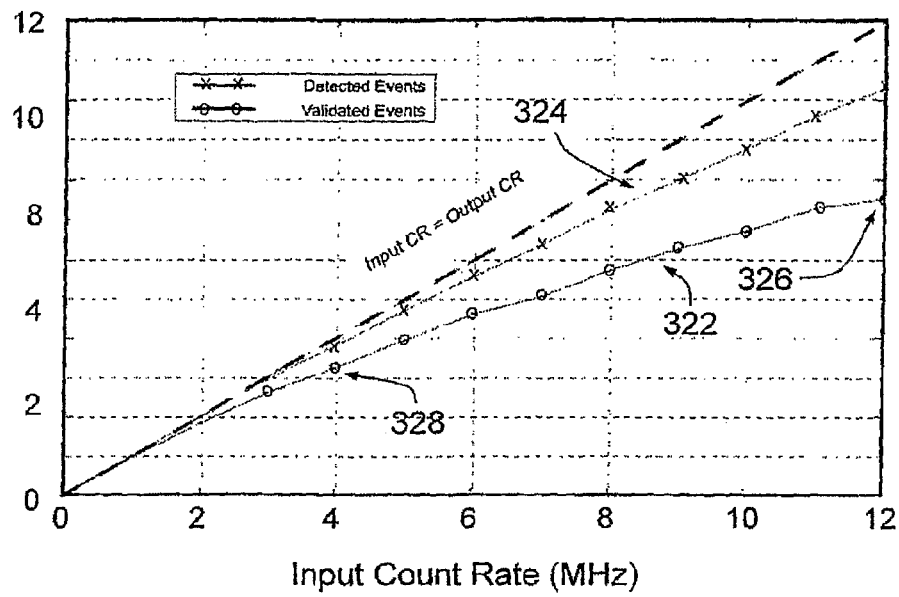
FIG. 24 is the plot, from a single detector pixel in the detector of the CT X-ray machine, of the calculated output count-rate performance of the signal processing method for pulse pile-up recovery of an embodiment of the present invention.

FIG. 24 is a plot of the throughput count rate (MHz) versus input count rate (MHz), calculated using the pulse characteristics depicted in FIG. 23. All events that pass the validation stage of the signal processing method for pulse pile-up recovery of this embodiment (based on that described above by reference to FIG. 9) 9 are plotted as circles; those events that are detected but fail the validation stage, that is, are deemed insufficiently accurately estimated, are plotted with crosses 324. It can be seen that, at an input count-rate of 12 MHz, the pile-up recovery algorithm of this embodiment is able to recovery accurately approximately 65% of all events (see point 326). At lower input count-rates, for example at point 328 where the input count-rate is 4 MHz, the percentage of events accurately recovered is approximately 80% of the input count-rate.

Figure 25:
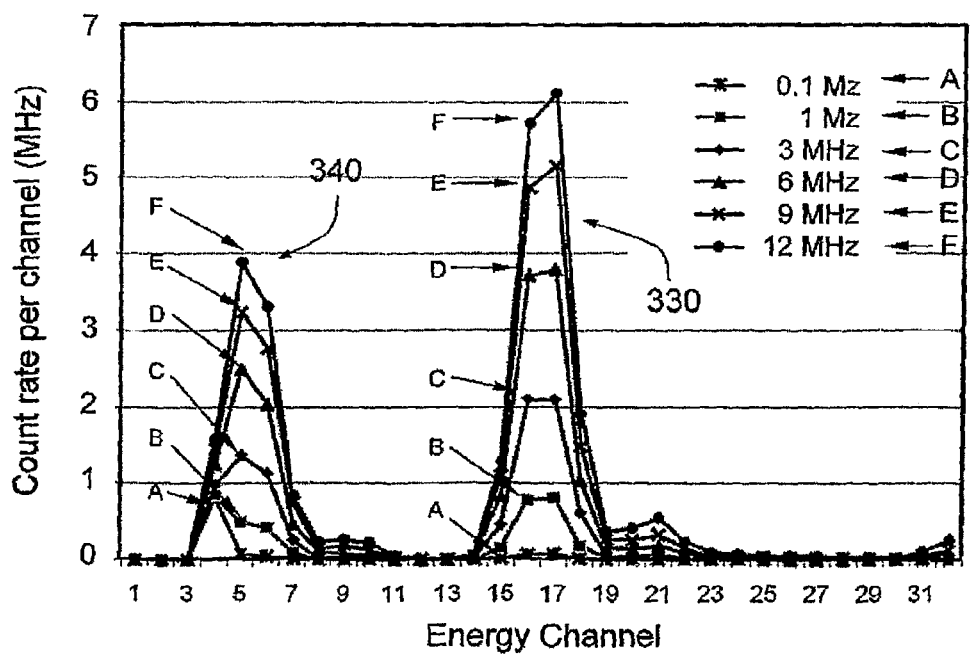
FIG. 25 is a plot of the calculated energy resolution performance, across a range of input count-rates, of the signal processing method for pulse pile-up recovery of an embodiment of the present invention.

FIG. 25 depicts the energy spectra produced by the pulse pile-up recovery algorithm at a range of input count rates 0.1 MHz, 1 MHz, 3 MHz, 6 MHz, 9 MHz and 12 MHz. Two energy peaks clearly visible in the energy spectra, a high energy peak 330 at energy channel 18, and a low energy peak 340 at energy channel 6. Despite the wide range of input count-rate, from 0.1 MHz to 12 MHz the signal processing method for pulse pile-up recovery of this embodiment is able to accurately detect the incoming radiation.

Modifications within the scope of the invention may be readily effected by those skilled in the art. It is to be understood, therefore, that this invention is not limited to the particular embodiments described by way of example hereinabove.

In the claims that follow and in the preceding description of the invention, except where the context requires otherwise owing to express language or necessary implication, the word "comprise" or variations such as "comprises" or "comprising" is used in an inclusive sense, i.e. to specify the presence of the stated features but not to preclude the presence or addition of further features in various embodiments of the invention.

Further, any reference herein to prior art is not intended to imply that such prior art forms or formed a part of the common general knowledge.

The invention claimed is:

1. An imaging method, comprising:
    collecting detector output data at an input count rate from a radiation detector that is positioned to view a subject provided with a radio-active tracer; and
    resolving by a processor individual signals in the detector output data to generate image signals at a throughput count rate, resolving the individual signals comprising:
        determining a signal form of said signals present in said detector output data,
        making parameter estimates of one or more parameters of said signals, wherein said one or more parameters comprise at least one signal temporal position,
        determining energy of each of said signals from at least said signal form and said parameter estimates, and
        maintaining the input count rate at or below a threshold input count rate, wherein the throughput count rate decreases for an input count rate value that is above the threshold input count rate, and wherein the throughput count rate decreases as an input count rate value that is below the threshold input count rate decreases.

2. A method as claimed in claim 1, wherein resolving of individual signals comprises:
    digitizing said detector output data to digitized detector output data in a form of a digital time series; and
    forming a mathematical model based on the digital time series as a function of at least the signal form, the signal temporal position of the signals, and at least one amplitude of the signals,
    wherein determining the energy of each of said signals comprises determining the amplitude of said signals based on said mathematical model, the amplitude being indicative of a radiation event.

3. A method as claimed in claim 1 further comprising reducing scanning time or tracer dose by between 5% and 30%.

4. A method as claimed in claim 1 further comprising gating the detector output data according to an output of another radiation detector.

5. A method as claimed in claim 1 further comprising gating the detector output data according to an output of another radiation detector in a coincidence mode.

6. A method as claimed in claim 1, wherein collecting the detector output data comprises collecting the detector output data from a medical imaging detector.

7. A method as claimed in claim 1, wherein collecting the detector output data comprises collecting the detector output data from a tomography detector.

8. A method as claimed in claim 1, wherein collecting the detector output data comprises collecting the detector output data from a PET tomography detector.

9. A method as claimed in claim 1, wherein resolving of individual signals further comprises reducing scanning time per image or projection by 25% or more.

10. A method as claimed in claim 1, wherein resolving of individual signals further comprises reducing scanning time per image or projection by 35% or more.

11. A method as claimed in claim 1, wherein collecting the detector output data comprises collecting the detector output data from an incident flux on said radiation detector of gamma-rays, the incident flux on said radiation detector configured to be of 100 kHz or more.

12. A method as claimed in claim 1, wherein a data throughput of said radiation detector is configured to be greater than 90% for an input count rate of 50 kHz.

13. A method as claimed in claim 1, wherein a data throughput of said radiation detector is configured to be greater than 90% for input count rates between 25 kHz and 250 kHz.

14. A method as claimed in claim 1, wherein a data throughput of said radiation detector is configured to be greater than 95% for an input count rate of 25 kHz.

15. A method as claimed in claim 1, wherein a data throughput of said radiation detector is configured to be greater than 95% for input count rates between 25 and 100 kHz.

16. A method as claimed in claim 1, wherein a data throughput of said radiation detector is configured to be greater than 80% for an input count rate of 250 kHz.

17. A method as claimed in claim 1, wherein a data throughput of said radiation detector is configured to be greater than 50% for input count rates between 250 and 2500 kHz.

18. A method as claimed in claim 1, wherein collecting the detector output data comprises collecting the detector output data from a SPECT camera, a scan time per projection or image of collecting the detector output data from the SPECT camera configured to be no more than 15 s.

19. A method as claimed in claim 1, wherein collecting detector output data comprises collecting detector output data from a SPECT camera, a scan time per projection or image of collecting the detector output data from the SPECT camera configured to be no more than 13 s.

20. A method as claimed in claim 1, wherein resolving individual signals further comprises generating image signals of a higher resolution.

21. A method as claimed in claim 1, wherein maintaining the input count rate further comprises maintaining the input count rate between 9 kHz and 90 kHz.

22. An imaging apparatus, comprising:
 a first radiation detector positioned to view a subject provided with a radio-active tracer, for detecting radiation emitted by the radio-active tracer, and for outputting detector data at an count rate in response thereto; and
 a processor for receiving the detector data in a digitized form to generate image signals at a throughput count rate, the processor configured to:
  determine a signal form of signals present in the detector data,
  make parameter estimates of one or more parameters of the signals,
  determine energy of each of the signals from at least the signal form and the parameter estimates, wherein the one or more parameters comprise at least one signal temporal position, and
  maintain the input count rate at or below a threshold input count rate, wherein the throughput count rate decreases for an input count rate value that is above the threshold input count rate, and wherein the throughput count rate decreases as an input count rate value that is below the threshold input count rate decreases.

23. An apparatus as claimed in claim 22, wherein said processor is further configured to:
 obtain said detector output data in a form of a digital time series, and
 form a mathematical model based on the digital time series as a function of at
 least the signal form, the signal temporal position of said signals, and at least one
 amplitude of said signals,
 wherein determining the energy of each of said signals comprises determining the amplitude of said signals based on said mathematical model, the amplitude being indicative of a radiation event.

24. An apparatus as claimed in claim 22, including one or more second radiation detectors, wherein the apparatus is configured to gate the detector data of the first radiation detector according to detector data of one or more of the second radiation detectors.

25. An apparatus as claimed in claim 24, wherein the apparatus is further configured to gate the detector data of the first radiation detector according to detector data of one or more of the second radiation detectors in a coincidence mode.

26. An apparatus as claimed in claim 22, wherein the processor is coupled to a medical imaging device and is configure to receive the detector data from the medical imaging apparatus.

27. An apparatus as claimed in claim 22, wherein the processor is coupled to the tomography apparatus and is configured to receive the detector data from the tomography apparatus.

28. An apparatus as claimed in claim 22, wherein the processor is coupled to the PET apparatus and is configured to receive the detector data from the PET apparatus.

29. An apparatus as claimed in claim 22, wherein said processor is configured to reduce scanning time per image or projection by 25% or more.

30. An apparatus as claimed in claim 22, wherein said processor is configured to reduce scanning time per image or projection by 35% or more.

31. An apparatus as claimed in claim 22, wherein the processor is further configured to generate image signals of a higher resolution.

32. An apparatus as claimed in claim 22, wherein the processor is further configured to maintain the input count rate between 9 kHz and 90 kHz.

* * * * *